United States Patent
Jha et al.

(10) Patent No.: US 10,954,275 B1
(45) Date of Patent: Mar. 23, 2021

(54) DESIGNED PROTEINS FOR PH SWITCHABLE ANTIBODY PURIFICATION

(71) Applicant: Los Alamos National Security, LLC, Los Alamos, NM (US)

(72) Inventors: Ramesh Jha, Los Alamos, NM (US); Charlie Strauss, Los Alamos, NM (US); Andrew M. Bradbury, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 224 days.

(21) Appl. No.: 16/054,882

(22) Filed: Aug. 3, 2018

Related U.S. Application Data

(60) Provisional application No. 62/541,414, filed on Aug. 4, 2017.

(51) Int. Cl.
  *C07K 14/315* (2006.01)
  *C07K 1/14* (2006.01)

(52) U.S. Cl.
  CPC ............. *C07K 14/315* (2013.01); *C07K 1/14* (2013.01)

(58) Field of Classification Search
  None
  See application file for complete search history.

(56) References Cited

U.S. PATENT DOCUMENTS

2015/0037312 A1   2/2015   Baker et al.

FOREIGN PATENT DOCUMENTS

WO   WO 2013/148583 A1   10/2013
WO   WO 2016/061427 A1   4/2016

OTHER PUBLICATIONS

Jha et al. An improved Protein G with higher affinity for human/rabbit IgG Fc domains exploiting a computationally designed polar network. Protein Engineering, Design & Selection vol. 27 No. 4 pp. 127-134, 2014.*
GenBank: KKC18279.1. immunoglobulin G-binding protein G [*Streptococcus dysgalactiae* subsp. equisimilis]. Dated Apr. 8, 2015.*
Lu et al. A Novel Immunoprecipitation Strategy Identifies a Unique Functional Mimic of the Glial Cell Line-Derived Neurotrophic Factor Family Ligands in the Pathogen Trypanosoma cruzi. Infection and Immunity, Aug. 2008, p. 3530-3538.*
Bailey et al., "Applications for an engineered Protein-G variant with a pH controllable affinity to antibody fragments," *J. Immunological Meth.*, vol. 415, pp. 24-30, 2014.
Ferrara et al., "Fluorescent Labeling of Antibody Fragments Using Split GFP," *PLoS ONE* 6:e25727, 2011 (9 pages).
Hess et al., "Rational protein design for pH switchable antibody purification tool," Poster presented at LANL Student Symposium, Los Alamos, NM on Aug. 3, 2016 (1 page).
Murphy et al., "Technology advancements in antibody purification," *Antibody Technology J.*, vol. 6, pp. 17-32, 2016.
Strauch et al, "Computational design of a pH-sensitive IgG binding protein," *PNAS*, vol. 111, No. 2, pp. 675-680, 2014.
Watanabe et al., "Optimizing pH Response of Affinity between Protein G and IgG Fc: How electrostatic modulations affect protein-protein interactions." *Journal of Biological Chemistry*, vol. 284, No. 18, pp. 12373-12383, 2009.

* cited by examiner

*Primary Examiner* — Nianxiang Zou
(74) *Attorney, Agent, or Firm* — Klarquist Sparkman, LLP

(57) ABSTRACT

Modified Fc-binding domain polypeptides or polypeptides including one or more modified Fc-binding domains are provided. In some examples, a modified Fc-binding domain includes or consists of the amino acid sequence of any one of SEQ ID NOs: 4, 6, or 8. Nucleic acids encoding the modified Fc-binding domains or polypeptides including one or more of the modified Fc-binding domains are also provided. In some embodiments, the nucleic acids are included in a vector and may be operably linked to a promoter. Methods for purifying a polypeptide including one or more Fc regions are also provided. Kits and reagents including the modified Fc-binding domain polypeptides or polypeptides including one or more modified Fc-binding domains are provided. In some examples, the modified Fc-binding domain polypeptides or polypeptides including one or more modified Fc-binding domains are linked to a solid support.

20 Claims, 9 Drawing Sheets

Specification includes a Sequence Listing.

FIG. 10

```
C1_domain  1  DTYKLNGKTLKGETTTEAVDAATAEKVFKQYANDNGVDGEWTYDDAATKTFTVTE
C2_domain  1  TTYKLVINGKTLKGETTTEAVDAATAEKVFKQYANDNGVDGEWTYDDAATKTFTVTE
C3_domain  1  TTYKLVINGKTLKGETTTKAVDAETAEKAFKQYANDNGVDGVWTYDDAATKTFTVTE
```

DESIGNED PROTEINS FOR PH SWITCHABLE ANTIBODY PURIFICATION

CROSS REFERENCE TO RELATED APPLICATION

This application claims the benefit of U.S. Provisional Patent Application No. 62/541,414, filed on Aug. 4, 2017, which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

This disclosure relates to polypeptides including modified Fc-binding domains, particularly modified C domains of Protein G, and methods for their use.

BACKGROUND

Immunoglobulin binding proteins (IBPs), such as Protein A and Protein G are widely utilized as reagents for the purification and detection of antibodies. Protein G consists of three Fc-binding domains (C1, C2 and C3), as well as an albumin binding portion. The Fc domain is common to all antibodies and plays a role in antibody effector function, signaling, and antibody fate. The Fc-binding property of Protein G has led to numerous biotechnological applications of Protein G as an affinity reagent. These include antibody purification or detection, siRNA delivery, and immuno-rolling circle amplification. Higher affinity variants of Protein G's Fc-binding domain would significantly enhance the biotechnological utility of this potent reagent. In addition, the common techniques for purification of antibodies include loading a mixture of proteins onto a Protein G column at pH 7.0 and eluting the antibody from the column at pH 2.7, which is below the pKa of glutamic acid and aspartic acid, the polar amino acids that form salt bridges in proteins and are important for structural stability. However, eluting at this pH is potentially detrimental to both Protein G and antibody folding and stability.

SUMMARY

Therefore, there is a need for IBPs that have a higher affinity for the Fc domain. In addition, there is a need for purification techniques that use elution buffers closer to physiological pH. Described herein are modified Fc-binding domains and polypeptides (such as IBPs) including one or more modified Fc binding-domains engineered to have improved affinity for Fc regions over the wild-type Fc-binding domain(s) and/or having decreased affinity for Fc regions at a mild acidic pH (e.g., ~6) compared to a more acidic (harsher) pH.

In some embodiments, the disclosure relates to modified Fc-binding domain polypeptides or polypeptides including one or more (such as 1, 2, or 3) modified Fc-binding domains. In some examples, a modified Fc-binding domain includes or consists of the amino acid sequence of any one of SEQ ID NOs: 4, 6, or 8. In further embodiments, a modified Fc-binding domain includes one or more (such as 1, 2, 3, or 4) amino acid substitutions selected from A24E, K28R, K28H, V29H, N35E, N35D, with numbering from the first amino acid of the Fc-binding domain, for example, amino acids corresponding to amino acid 302 (first amino acid of C1 domain), 372 (first amino acid of C2 domain), or 442 (first amino acid of C3 domain) of SEQ ID NO: 1. In some examples, the modified Fc-binding domain does not include only A24E, K28R, and V29H amino acid substitutions. In other examples, the modified Fc-binding domain does not include each of A24E, K28R, and V29H amino acid substitutions, unless at least one other amino acid substitution is present.

In other embodiments, a polypeptide including a modified Fc-binding domain includes at least one modified Fc-binding domain including or consisting of the sequence of one of SEQ ID NOs: 4, 6, or 8. In additional examples, a polypeptide including one or more modified Fc-binding domains includes an amino acid sequence with at least 90% identity to SEQ ID NO: 2, for example, any one of SEQ ID NOs: 10-12. In some examples, the immunoglobulin-binding protein has at least 10-fold higher affinity for human IgG at pH 5.6 than at pH 8.2.

Also disclosed are nucleic acids encoding the modified Fc-binding domains or encoding the polypeptides including one or more of the modified Fc-binding domains. In some examples, a nucleic acid encoding the modified Fc-binding domain includes or consists of the nucleic acid sequence of any one of SEQ ID NOs: 3, 5, or 7. In other examples, a nucleic acid encoding a polypeptide including one or more of the modified Fc-binding domains includes or consists of the nucleic acid sequence of any one of SEQ ID NOs: 13-15. In some embodiments, the disclosed nucleic acids are included in a vector and may be operably linked to a promoter.

Methods for purifying a polypeptide including one or more Fc regions are also disclosed. In some embodiments, the method includes contacting a modified Fc-binding domain polypeptide or a polypeptide including one or more modified Fc-binding domains with a polypeptide including one or more Fc regions at a pH of about 6 or less to form a complex of the modified Fc-binding domain or the polypeptide including one or more modified Fc-binding domains and the polypeptide including one or more Fc regions; and contacting the complex with a buffer at a basic pH (e.g., about pH 8 or above) to dissociate the polypeptide including one or more Fc regions.

Also disclosed are kits and reagents including the modified Fc-binding domain polypeptides or the polypeptides including one or more modified Fc-binding domains. In some examples, the modified Fc-binding domain polypeptides or the polypeptides including one or more modified Fc-binding domains are linked to a solid support. In one example, the modified Fc-binding domain polypeptides or the polypeptides including one or more modified Fc-binding domains linked to a solid support are included in a column, such as an affinity purification column. The modified Fc-binding domain polypeptides or the polypeptides including one or more modified Fc-binding domains linked to a solid support may also be included in a kit with one or more buffers, such as a buffer with pH about 8.

The foregoing and other features of the disclosure will become more apparent from the following detailed description, which proceeds with reference to the accompanying figures.

BRIEF DESCRIPTION OF THE DRAWINGS

FIG. 10 is an alignment of the C1, C2, and C3 domains from protein G from *Streptococcus* sp. (amino acids 302-357, 372-427, and 442-497 of SEQ ID NO: 1, respectively).

SEQUENCE LISTING

Figure 1:
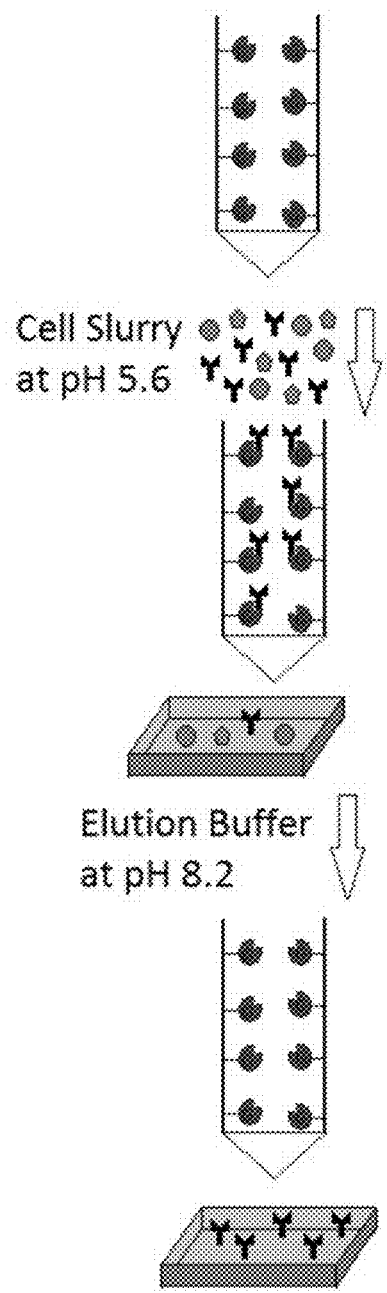
FIG. 1 is a schematic diagram showing an exemplary method of purifying an antibody using a column with modified Protein G. Proteins are applied to the column in a buffer at pH 5.6 under which conditions the antibody binds to the Protein G. Elution is carried out at pH 8.2.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Aug. 3, 2018, and is 31.7 Kbytes, which is incorporated by reference herein.

SEQ ID NO: 1 is the amino acid sequence of a full length Protein G from *Streptococcus* sp.:

MEKEKKVKYFLRKSAFGLASVSAAFLVGSTVFAVDSPIEDTPIIRNGGEL

TNLLGNSETTLALRNEESATADLTAAAVADTVAAAAENAGAAAWEAAAA

ADALAKAKADALKEFNKYGVSDYYKNLINNAKTVEGVKDLQAQVVESAKK

ARISEATDGLSDFLKSQTPAEDTVKSIELAEAKVLANRELDKYGVSDYHK

NLINNAKTVEGVKDLQAQVVESAKKARISEATDGLSDFLKSQTPAEDTVK

SIELAEAKVLANRELDKYGVSDYYKNLINNAKTVEGVKALIDEILAALPK

TDTYKLILNGKTLKGETTTEAVDAATAEKVFKQYANDNGVDGEWTYDDAT

KTFTVTEKPEVIDASELTPAVTTYKLVINGKTLKGETTTEAVDAATAEKV

FKQYANDNGVDGEWTYDDATKTFTVTEKPEVIDASELTPAVTTYKLVING

KTLKGETTTKAVDAETAEKAFKQYANDNGVDGVWTYDDATKTFTVTEMVT

EVPGDAPTEPEKPEASIPLVPLTPATPIAKDDAKKDDTKKEDAKKPEAKK

EDAKKAETLPTTGEGSNPFFTAAALAVMAGAGALAVASKRKED

The IgG binding domains (C1, C2, and C3) are underlined. The C2 domain is shown in bold type.

SEQ ID NO: 2 is the amino acid sequence of a wild type Protein G C2 domain:

TTYKLVINGKTLKGETTTEAVDAATAEKVFKQYANDNGVDGEWTYDDATK

TFTVTE

SEQ ID NO: 3 is a nucleic acid sequence encoding a Protein G EHH C2 domain:

ACAACCTATAAATTAGTCATAAACGGTAAAACATTGAAGGGTGAAACCAC

AACTGAAGCTGTAGACGCCGAAACTGCTGAACACCATTTTAAACAATATG

CTAATGATAATGGTGTAGATGGTGAATGGACCTATGATGACGCCACTAAG

ACCTTTACTGTTACTGAA

SEQ ID NO: 4 is the amino acid sequence of a Protein G EHH C2 domain (mutated residues are underlined):

TTYKLVINGKTLKGETTTEAVDA<u>E</u>TAE<u>HH</u>FKQYANDNGVDGEWTYDDATK

TFTVTE

SEQ ID NO: 5 is a nucleic acid sequence encoding a Protein G EHHE C2 domain:

ACAACCTATAAATTAGTCATAAACGGTAAAACATTGAAGGGTGAAACCAC

AACTGAAGCTGTAGACGCCGAAACTGCTGAACACCATTTTAAACAATATG

CTGAAGATAATGGTGTAGATGGTGAATGGACCTATGATGACGCCACTAAG

ACCTTTACTGTTACTGAA

SEQ ID NO: 6 is the amino acid sequence of a Protein G EHHE C2 domain (mutated residues are underlined):

TTYKLVINGKTLKGETTTEAVDA<u>E</u>TAE<u>HH</u>FKQYA<u>E</u>DNGVDGEWTYDDATK

TFTVTE

SEQ ID NO: 7 is a nucleic acid sequence encoding a Protein G EHHD C2 domain:

ACAACCTATAAATTAGTCATAAACGGTAAAACATTGAAGGGTGAAACCAC

AACTGAAGCTGTAGACGCCGAAACTGCTGAACACCATTTTAAACAATATG

-continued

CTGACGATAATGGTGTAGATGGTGAATGGACCTATGATGACGCCACTAAA

ACCTTTACTGTTACTGAA

SEQ ID NO: 8 is the amino acid sequence of a Protein G EHHD C2 domain (mutated residues are underlined):

TTYKLVINGKTLKGETTTEAVDAETAEHHFKQYADDNGVDGEWTYDDATK

TFTVTE

SEQ ID NO: 9 is the amino acid sequence of a Protein G ERH C2 domain (mutated residues are underlined):

TTYKLVINGKTLKGETTTEAVDAETAERHFKQYANDNGVDGEWTYDDATK

TFTVTE

SEQ ID NO: 10 is the amino acid sequence of an exemplary Protein G EHH variant (mutated residues are underlined):

MEKEKKVKYFLRKSAFGLASVSAAFLVGSTVFAVDSPIEDTPIIRNGGEL

TNLLGNSETTLALRNEESATADLTAAAVADTVAAAAAENAGAAAWEAAAA

ADALAKAKADALKEFNKYGVSDYYKNLINNAKTVEGVKDLQAQVVESAKK

ARISEATDGLSDFLKSQTPAEDTVKSIELAEAKVLANRELDKYGVSDYHK

NLINNAKTVEGVKDLQAQVVESAKKARISEATDGLSDFLKSQTPAEDTVK

SIELAEAKVLANRELDKYGVSDYYKNLINNAKTVEGVKALIDEILAALPK

TDTYKLILNGKTLKGETTTEAVDAETAEHHFKQYANDNGVDGEWTYDDAT

KTFTVTEKPEVIDASELTPAVTTYKLVINGKTLKGETTTEAVDAETAEHH

FKQYANDNGVDGEWTYDDATKTFTVTEKPEVIDASELTPAVTTYKLVING

KTLKGETTTKAVDAETAEHHFKQYANDNGVDGVWTYDDATKTFTVTEMVT

EVPGDAPTEPEKPEASIPLVPLTPATPIAKDDAKKDDTKKEDAKKPEAKK

EDAKKAETLPTTGEGSNPFFTAAALAVMAGAGALAVASKRKED

SEQ ID NO: 11 is the amino acid sequence of an exemplary Protein G EHHE variant (mutated residues are underlined):

MEKEKKVKYFLRKSAFGLASVSAAFLVGSTVFAVDSPIEDTPIIRNGGEL

TNLLGNSETTLALRNEESATADLTAAAVADTVAAAAAENAGAAAWEAAAA

ADALAKAKADALKEFNKYGVSDYYKNLINNAKTVEGVKDLQAQVVESAKK

ARISEATDGLSDFLKSQTPAEDTVKSIELAEAKVLANRELDKYGVSDYHK

NLINNAKTVEGVKDLQAQVVESAKKARISEATDGLSDFLKSQTPAEDTVK

SIELAEAKVLANRELDKYGVSDYYKNLINNAKTVEGVKALIDEILAALPK

TDTYKLILNGKTLKGETTTEAVDAETAEHHFKQYAEDNGVDGEWTYDDAT

KTFTVTEKPEVIDASELTPAVTTYKLVINGKTLKGETTTEAVDAETAEHH

FKQYAEDNGVDGEWTYDDATKTFTVTEKPEVIDASELTPAVTTYKLVING

KTLKGETTTKAVDAETAEHHFKQYAEDNGVDGVWTYDDATKTFTVTEMVT

EVPGDAPTEPEKPEASIPLVPLTPATPIAKDDAKKDDTKKEDAKKPEAKK

EDAKKAETLPTTGEGSNPFFTAAALAVMAGAGALAVASKRKED

SEQ ID NO: 12 is the amino acid sequence of an exemplary Protein G EHHD variant (mutated residues are underlined):

MEKEKKVKYFLRKSAFGLASVSAAFLVGSTVFAVDSPIEDTPIIRNGGEL

TNLLGNSETTLALRNEESATADLTAAAVADTVAAAAAENAGAAAWEAAAA

ADALAKAKADALKEFNKYGVSDYYKNLINNAKTVEGVKDLQAQVVESAKK

ARISEATDGLSDFLKSQTPAEDTVKSIELAEAKVLANRELDKYGVSDYHK

NLINNAKTVEGVKDLQAQVVESAKKARISEATDGLSDFLKSQTPAEDTVK

SIELAEAKVLANRELDKYGVSDYYKNLINNAKTVEGVKALIDEILAALPK

TDTYKLILNGKTLKGETTTEAVDAETAEHHFKQYADDNGVDGEWTYDDAT

KTFTVTEKPEVIDASELTPAVTTYKLVINGKTLKGETTTEAVDAETAEHH

FKQYADDNGVDGEWTYDDATKTFTVTEKPEVIDASELTPAVTTYKLVING

KTLKGETTTKAVDAETAEHHFKQYADDNGVDGVWTYDDATKTFTVTEMVT

EVPGDAPTEPEKPEASIPLVPLTPATPIAKDDAKKDDTKKEDAKKPEAKK

EDAKKAETLPTTGEGSNPFFTAAALAVMAGAGALAVASKRKED

SEQ ID NO: 13 is an exemplary nucleic acid sequence encoding a Protein G EHH variant:

ATGGAAAAAGAAAAAAAGTGAAATATTTTCTGCGCAAAAGCGCGTTTGG

CCTGGCGAGCGTGAGCGCGGCGTTTCTGGTGGGCAGCACCGTGTTTGCGG

TGGATAGCCCGATTGAAGATACCCCGATTATTCGCAACGGCGGCGAACTG

ACCAACCTGCTGGGCAACAGCGAAACCACCCTGGCGCTGCGCAACGAAGA

AAGCGCGACCGCGGATCTGACCGCGGCGGCGGTGGCGGATACCGTGGCGG

CGGCGGCGGCGGAAAACGCGGGCGCGGCGGCGTGGGAAGCGGCGGCGGCG

GCGGATGCGCTGGCGAAAGCGAAAGCGGATGCGCTGAAAGAATTTAACAA

ATATGGCGTGAGCGATTATTATAAAAACCTGATTAACAACGCGAAAACCG

TGGAAGGCGTGAAAGATCTGCAGGCGCAGGTGGTGGAAAGCGCGAAAAAA

GCGCGCATTAGCGAAGCGACCGATGGCCTGAGCGATTTTCTGAAAAGCCA

GACCCCGGCGGAAGATACCGTGAAAAGCATTGAACTGGCGGAAGCGAAAG

TGCTGGCGAACCGCGAACTGGATAAATATGGCGTGAGCGATTATCATAAA

AACCTGATTAACAACGCGAAAACCGTGGAAGGCGTGAAAGATCTGCAGGC

GCAGGTGGTGGAAAGCGCGAAAAAAGCGCGCATTAGCGAAGCGACCGATG

GCCTGAGCGATTTTCTGAAAAGCCAGACCCCGGCGGAAGATACCGTGAAA

AGCATTGAACTGGCGGAAGCGAAAGTGCTGGCGAACCGCGAACTGGATAA

ATATGGCGTGAGCGATTATTATAAAAACCTGATTAACAACGCGAAAACCG

TGGAAGGCGTGAAAGCGCTGATTGATGAAATTCTGGCGGCGCTGCCGAAA

ACCGATACCTATAAACTGATTCTGAACGGCAAAACCCTGAAAGGCGAAAC

CACCACCGAAGCGGTGGATGCGGAAACCGCGGAACATCATTTTAAACAGT

-continued

```
ATGCGAACGATAACGGCGTGGATGGCGAATGGACCTATGATGATGCGACC
AAAACCTTTACCGTGACCGAAAAACCGGAAGTGATTGATGCGAGCGAACT
GACCCCGGCGGTGACCACCTATAAACTGGTGATTAACGGCAAAACCCTGA
AAGGCGAAACCACCACCGAAGCGGTGGATGCGGAAACCGCGGAACATCAT
TTTAAACAGTATGCGAACGATAACGGCGTGGATGGCGAATGGACCTATGA
TGATGCGACCAAAACCTTTACCGTGACCGAAAAACCGGAAGTGATTGATG
CGAGCGAACTGACCCCGGCGGTGACCACCTATAAACTGGTGATTAACGGC
AAAACCCTGAAAGGCGAAACCACCACCAAAGCGGTGGATGCGGAAACCGC
GGAACATCATTTTAAACAGTATGCGAACGATAACGGCGTGGATGGCGTGT
GGACCTATGATGATGCGACCAAAACCTTTACCGTGACCGAAATGGTGACC
GAAGTGCCGGGCGATGCGCCGACCGAACCGGAAAAACCGGAAGCGAGCAT
TCCGCTGGTGCCGCTGACCCCGGCGACCCCGATTGCGAAAGATGATGCGA
AAAAGATGATACCAAAAAGAAGATGCGAAAAAACCGGAAGCGAAAAAA
GAAGATGCGAAAAAAGCGGAAACCCTGCCGACCACCGGCGAAGGCAGCAA
CCCGTTTTTTACCGCGGCGGCGCTGGCGGTGATGGCGGGCGCGGGCGCGC
TGGCGGTGGCGAGCAAACGCAAAGAAGAT
```

SEQ ID NO: 14 is an exemplary nucleic acid sequence encoding a Protein G EHHE variant:

```
ATGGAAAAAGAAAAAAAAGTGAAATATTTTCTGCGCAAAAGCGCGTTTGG
CCTGGCGAGCGTGAGCGCGGCGTTTCTGGTGGGCAGCACCGTGTTTGCGG
TGGATAGCCCGATTGAAGATACCCCGATTATTCGCAACGGCGGCGAACTG
ACCAACCTGCTGGGCAACAGCGAAACCACCCTGGCGCTGCGCAACGAAGA
AAGCGCGACCGCGGATCTGACCGCGGCGGCGGTGGCGGATACCGTGGCGG
CGGCGGCGGCGGAAAACGCGGGCGCGGCGGCGTGGGAAGCGGCGGCGGCG
GCGGATGCGCTGGCGAAAGCGAAAGCGGATGCGCTGAAAGAATTTAACAA
ATATGGCGTGAGCGATTATTATAAAAACCTGATTAACAACGCGAAAACCG
TGGAAGGCGTGAAAGATCTGCAGGCGCAGGTGGTGGAAAGCGCGAAAAAA
GCGCGCATTAGCGAAGCGACCGATGGCCTGAGCGATTTTCTGAAAAGCCA
GACCCCGGCGGAAGATACCGTGAAAAGCATTGAACTGGCGGAAGCGAAAG
TGCTGGCGAACCGCGAACTGGATAAATATGGCGTGAGCGATTATCATAAA
AACCTGATTAACAACGCGAAAACCGTGGAAGGCGTGAAAGATCTGCAGGC
GCAGGTGGTGGAAAGCGCGAAAAAAGCGCGCATTAGCGAAGCGACCGATG
GCCTGAGCGATTTTCTGAAAAGCCAGACCCCGGCGGAAGATACCGTGAAA
AGCATTGAACTGGCGGAAGCGAAAGTGCTGGCGAACCGCGAACTGGATAA
ATATGGCGTGAGCGATTATTATAAAAACCTGATTAACAACGCGAAAACCG
TGGAAGGCGTGAAAGCGCTGATTGATGAAATTCTGGCGGCGCTGCCGAAA
ACCGATACCTATAAACTGATTCTGAACGGCAAAACCCTGAAAGGCGAAAC
CACCACCGAAGCGGTGGATGCGGAAACCGCGGAACATCATTTTAAACAGT
ATGCGGAAGATAACGGCGTGGATGGCGAATGGACCTATGATGATGCGACC
AAAACCTTTACCGTGACCGAAAAACCGGAAGTGATTGATGCGAGCGAACT
```

-continued

```
GACCCCGGCGGTGACCACCTATAAACTGGTGATTAACGGCAAAACCCTGA
AAGGCGAAACCACCACCGAAGCGGTGGATGCGGAAACCGCGGAACATCAT
TTTAAACAGTATGCGGAAGATAACGGCGTGGATGGCGAATGGACCTATGA
TGATGCGACCAAAACCTTTACCGTGACCGAAAAACCGGAAGTGATTGATG
CGAGCGAACTGACCCCGGCGGTGACCACCTATAAACTGGTGATTAACGGC
AAAACCCTGAAAGGCGAAACCACCACCAAAGCGGTGGATGCGGAAACCGC
GGAACATCATTTTAAACAGTATGCGGAAGATAACGGCGTGGATGGCGTGT
GGACCTATGATGATGCGACCAAAACCTTTACCGTGACCGAAATGGTGACC
GAAGTGCCGGGCGATGCGCCGACCGAACCGGAAAAACCGGAAGCGAGCAT
TCCGCTGGTGCCGCTGACCCCGGCGACCCCGATTGCGAAAGATGATGCGA
AAAAGATGATACCAAAAAGAAGATGCGAAAAAACCGGAAGCGAAAAAA
GAAGATGCGAAAAAAGCGGAAACCCTGCCGACCACCGGCGAAGGCAGCAA
CCCGTTTTTTACCGCGGCGGCGCTGGCGGTGATGGCGGGCGCGGGCGCGC
TGGCGGTGGCGAGCAAACGCAAAGAAGAT
```

SEQ ID NO: 15 is an exemplary nucleic acid sequence encoding a Protein G EHHD variant:

```
ATGGAAAAAGAAAAAAAAGTGAAATATTTTCTGCGCAAAAGCGCGTTTGG
CCTGGCGAGCGTGAGCGCGGCGTTTCTGGTGGGCAGCACCGTGTTTGCGG
TGGATAGCCCGATTGAAGATACCCCGATTATTCGCAACGGCGGCGAACTG
ACCAACCTGCTGGGCAACAGCGAAACCACCCTGGCGCTGCGCAACGAAGA
AAGCGCGACCGCGGATCTGACCGCGGCGGCGGTGGCGGATACCGTGGCGG
CGGCGGCGGCGGAAAACGCGGGCGCGGCGGCGTGGGAAGCGGCGGCGGCG
GCGGATGCGCTGGCGAAAGCGAAAGCGGATGCGCTGAAAGAATTTAACAA
ATATGGCGTGAGCGATTATTATAAAAACCTGATTAACAACGCGAAAACCG
TGGAAGGCGTGAAAGATCTGCAGGCGCAGGTGGTGGAAAGCGCGAAAAAA
GCGCGCATTAGCGAAGCGACCGATGGCCTGAGCGATTTTCTGAAAAGCCA
GACCCCGGCGGAAGATACCGTGAAAAGCATTGAACTGGCGGAAGCGAAAG
TGCTGGCGAACCGCGAACTGGATAAATATGGCGTGAGCGATTATCATAAA
AACCTGATTAACAACGCGAAAACCGTGGAAGGCGTGAAAGATCTGCAGGC
GCAGGTGGTGGAAAGCGCGAAAAAAGCGCGCATTAGCGAAGCGACCGATG
GCCTGAGCGATTTTCTGAAAAGCCAGACCCCGGCGGAAGATACCGTGAAA
AGCATTGAACTGGCGGAAGCGAAAGTGCTGGCGAACCGCGAACTGGATAA
ATATGGCGTGAGCGATTATTATAAAAACCTGATTAACAACGCGAAAACCG
TGGAAGGCGTGAAAGCGCTGATTGATGAAATTCTGGCGGCGCTGCCGAAA
ACCGATACCTATAAACTGATTCTGAACGGCAAAACCCTGAAAGGCGAAAC
CACCACCGAAGCGGTGGATGCGGAAACCGCGGAACATCATTTTAAACAGT
ATGCGGATGATAACGGCGTGGATGGCGAATGGACCTATGATGATGCGACC
AAAACCTTTACCGTGACCGAAAAACCGGAAGTGATTGATGCGAGCGAACT
GACCCCGGCGGTGACCACCTATAAACTGGTGATTAACGGCAAAACCCTGA
AAGGCGAAACCACCACCGAAGCGGTGGATGCGGAAACCGCGGAACATCAT
```

```
                          -continued
TTTAAACAGTATGCGGATGATAACGGCGTGGATGGCGAATGGACCTATGA

TGATGCGACCAAAACCTTTACCGTGACCGAAAAACCGGAAGTGATTGATG

CGAGCGAACTGACCCCGGCGGTGACCACCTATAAACTGGTGATTAACGGC

AAAACCCTGAAAGGCGAAACCACCACCAAAGCGGTGGATGCGGAAACCGC

GGAACATCATTTTAAACAGTATGCGGATGATAACGGCGTGGATGGCGTGT

GGACCTATGATGATGCGACCAAAACCTTTACCGTGACCGAAATGGTGACC

GAAGTGCCGGGCGATGCGCCGACCGAACCGGAAAAACCGGAAGCGAGCAT

TCCGCTGGTGCCGCTGACCCCGGCGACCCCGATTGCGAAAGATGATGCGA

AAAAAGATGATACCAAAAAAGAAGATGCGAAAAAACCGGAAGCGAAAAAA

GAAGATGCGAAAAAAGCGGAAACCCTGCCGACCACCGGCGAAGGCAGCAA

CCCGTTTTTTACCGCGGCGGCGCTGGCGGTGATGGCGGGCGCGGGCGCGC

TGGCGGTGGCGAGCAAACGCAAAGAAGAT
```

DETAILED DESCRIPTION

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), Molecular Biology and Biotechnology: a Comprehensive Desk Reference, published by Wiley, John & Sons, Inc., 1995 (ISBN 0471186341); and George P. Rédei, *Encyclopedic Dictionary of Genetics, Genomics, Proteomics and Informatics*, 3$^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Antibody: A polypeptide that includes at least a light chain or a heavy chain immunoglobulin variable region and specifically binds an epitope of an antigen. Antibodies can include monoclonal antibodies, polyclonal antibodies, or fragments of antibodies. In some examples, an antibody is labeled with a detectable label such as an enzyme or a fluorophore.

Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and variants and portions of them, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies).

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Domain: A discrete part of an amino acid sequence of a polypeptide or protein that can be equated with a particular function. For example, IBPs include portions (such as C domains) that can bind to Fc regions of an antibody. The precise number of amino acids in the domain varies depending on the species, as well as between classes of genes within a species. An important aspect for selection of a sequence for use in a recombinant molecule is the maintenance of the domain function rather than a precise structural definition based on the number of amino acids. One of ordinary skill in the art will appreciate that domain function may be maintained even if somewhat less than the entire amino acid sequence of the selected domain is utilized.

Fc-Binding Domain: A polypeptide or portion thereof that binds the Fc region of an antibody. The Fc region (fragment crystallizable region) is the stalk region of an antibody that interacts with cell surface receptors called Fc receptors and some proteins of the complement system. Exemplary Fc-binding domains include the C1, C2, and C3 domains of Protein G, such as amino acids 302-357, 372-427, and 442-497 of SEQ ID NO: 1, respectively.

Immunoglobulin Binding Protein (IBP): A protein capable of specifically binding an immunoglobulin, such as IgG. Exemplary IBPs include Protein A and Protein G.

Isolated: An "isolated" biological component (such as a nucleic acid molecule, protein, or cell) has been substantially separated or purified away from other biological components, such as other chromosomal and extra-chromosomal DNA and RNA, proteins and/or cells. Nucleic acid molecules and proteins that have been "isolated" include nucleic acid molecules and proteins purified by standard purification methods or prepared by recombinant expression in a host cell, as well as chemically synthesized nucleic acid molecules and proteins.

Modified: A "modified" nucleic acid or polypeptide is one that has a sequence that is not naturally occurring or has a sequence that is made by an artificial combination of two or more otherwise separated segments of sequence. A modified nucleic acid or polypeptide is often produced by chemical synthesis or, more commonly, by the artificial manipulation of isolated segments of nucleic acids, e.g., by genetic engineering techniques, including but not limited to site-directed mutagenesis.

Purified: The term purified does not require absolute purity; rather, it is intended as a relative term. Thus, for example, a purified polypeptide is one in which the specified polypeptide is more enriched than it is in its original environment, for instance within a cell or other preparation. Preferably, a polypeptide is purified such that the specified polypeptide represents at least 50% of the total polypeptide content of the preparation. In some embodiments, a purified polypeptide contains at least 60%, at least 70%, at least 80%, at least 85%, at least 90%, at least 95% or more of the specified polypeptide.

Vector: A nucleic acid molecule that can be introduced into a host cell, thereby producing a transformed or trans-duced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in gram negative and gram positive bacterial cell. Exemplary vectors include those for use in *E. coli*. Vectors also include viral vectors, such as, but not limited to, retrovirus, orthopox, avipox, fowlpox, capripox, suipox, adenovirus, herpes virus, alpha virus, baculovirus, Sindbis virus, vaccinia virus, and polio-virus vectors. Vectors also include vectors for expression in yeast cells or mammalian cells.

II. Modified Binding Domains and Polypeptides

Disclosed herein are modified Fc-binding domains with increased affinity for Fc compared to a wild type Fc-binding domain and/or pH-switchable affinity at around physiological pH (e.g. pH ~6). In some embodiments, the Fc-binding domain (e.g., C domain) is any C domain from a Protein G. An exemplary Protein G amino acid sequence is provided herein as SEQ ID NO: 1. A "C" domain from Protein G (a wild type C domain) may include or consist of amino acids 302-357, 372-427, or 442-497 of SEQ ID NO: 1. In some embodiments a modified Fc-binding domain is a modified Protein G C2 domain that includes or consists of the amino acid sequence of any one of SEQ ID NOs: 4, 6, or 8. However, corresponding modifications in the C1 and/or C3 domains are also contemplated. An alignment of the C1, C2, and C3 domains of protein G from *Streptococcus* (SEQ ID NO: 1) is provided as FIG. 10.

In further embodiments, a modified Fc-binding domain includes one or more (such as 1, 2, 3, or 4) amino acid substitutions selected from A24E, K28R, K28H, V29H, N35E, N35D, with numbering from the first amino acid of the Fc-binding domain, for example, amino acids corresponding to amino acid 302 (C1 domain), 372 (C2 domain), or 442 (C3 domain) of SEQ ID NO: 1. In some examples, the modified Fc-binding domain includes each of A24E, K28H, and V29H amino acid substitutions. In other examples the modified Fc-binding domain includes each of A24E, K28H, V29H, and N35E amino acid substitutions. In further examples, the modified Fc-binding domain includes each of A24E, K28H, V29H, and N35D amino acid substitutions. In some examples, the modified Fc-binding domain does not include only A24E, K28R, and V29H amino acid substitutions. In other examples, the modified Fc-binding domain does not include each of A24E, K28R, and V29H amino acid substitutions, unless at least one other amino acid substitution is present.

Also disclosed herein are Protein G polypeptides that include one or more (such as 1, 2, or 3) modified Fc-binding domains. Exemplary Protein G polypeptides that include three modified C domains are provided in SEQ ID NOs: 10-12. Modified Protein G polypeptides with corresponding modifications in one of or two of the C1, C2, or C3 domains (e.g., a modified C2 domain only), as well as other combinations of modified domains are also contemplated. In some embodiments, the Protein G polypeptide further includes one or more additional amino acid substitutions outside of the Fc-binding domain(s). In one example, the Protein G includes a cysteine substitution (for example E56C). This substitution may be used because wild-type Lysine28 may be prone to bind to some resins, potentially masking the binding interface, and a cysteine mutation can reduce this interference.

In some embodiments, the modified Fc-binding domains disclosed herein, or the Protein G polypeptides including one or more modified Fc-binding domains, have at least a 1.5-fold increase in binding affinity for an Fc domain or a polypeptide including an Fc domain (such as an antibody or antibody fragment) below about pH 6, compared to a wild type Fc-binding domain or protein including one or more wild type Fc-binding domains. For example, the modified Fc-binding domain or the polypeptide including the modified Fc-binding domain(s) has a 1.5-fold to 10-fold increase in binding affinity, such as about 1.5- to 5-fold increase, about 2-fold to 4-fold increase, about 5-fold to 8-fold increase, or about 6-fold to 10-fold increase (for example, about 1.5-fold, 2-fold, 2.5-fold, 3-fold, 4-fold, 5-fold, 6-fold, 7-fold, 8-fold, 9-fold, or 10-fold increase) compared to a wild type Fc-binding domain or protein including one or more wild type Fc-binding domains. In particular examples, the polypeptide including one or more modified Fc-binding domains has at least 10-fold higher affinity (such as at least 10-fold, 20-fold, 30-fold, 40-fold, 50-fold or more higher affinity) for human IgG at pH 5.6 than at pH 8.2.

Methods of determining the affinity of an Fc-binding domain or a protein including one or more Fc-binding domains to an Fc domain or protein including an Fc domain are known to one of ordinary skill in the art. An exemplary method is described in Example 1, below. However, other methods of determining affinity, such as isothermal titration calorimetry, fluorescence polarization, or surface plasmon resonance, can also be used to determine binding affinity.

In other embodiments, the modified Fc-binding domains disclosed herein, or the Protein G polypeptides including one or more modified Fc-binding domains, have a pH-switchable affinity for an Fc domain or a protein containing one or more Fc domains that occurs at about pH 6. In some examples, the modified Fc-binding domain, or a polypeptide including one or more modified Fc-binding domains, has at least about 40% decreased affinity for an Fc domain or a protein containing one or more Fc domains above about pH 6.5 compared to the affinity below about pH 6. In some examples, the modified Fc-binding domain, or a polypeptide including one or more modified Fc-binding domains, has at least about 40%, 50%, 60%, 70%, 80%, 90%, 1.5-fold, 2-fold, 2.5-fold, 3-fold, 4-fold, 5-fold, 10-fold, 15-fold, 20-fold, 30-fold, 40-fold, 50-fold, or more (such as 40-100%, 2-5-fold, 4-10-fold, 7-15-fold, 12-20-fold, 15-30-fold, 20-40-fold, or 25-50-fold) decreased affinity for an Fc domain or a protein containing one or more Fc domains above about pH 6.5 compared to the affinity below about pH 6. In some examples, the modified Fc-binding domain, or a polypeptide including one or more modified Fc-binding domains, has about 20- to 40-fold decreased affinity for an Fc domain or a protein containing one or more Fc domains at about pH 8 (such as about pH 8 to pH 8.5) compared at about pH 6 (such as about pH 5.5 to pH 6). Methods of determining the affinity of an Fc-binding domain or protein including one or more Fc-binding domains for an Fc domain or protein including Fc domain(s) are discussed above. These methods can be performed at different pH (for example using buffers of different pH) in order to assess the affinity at different pH conditions.

Also disclosed herein are nucleic acids encoding the modified Fc-binding domains or polypeptides including one or more modified Fc-binding domains. In some examples, a nucleic acid encoding a modified Fc-binding domain includes or consists of the nucleic acid sequence of SEQ ID NO: 3, SEQ ID NO: 5, or SEQ ID NO: 7. In other examples, a polypeptide including one or more modified Fc-binding domains includes a modified Fc-binding domain encoded by the nucleic acid sequence of SEQ ID NO: 3, SEQ ID NO: 5, or SEQ ID NO: 7. In some examples, the nucleic acid encoding a polypeptide including one or more modified Fc-binding domains includes or consists of the nucleic acid sequence of one or more of SEQ ID NOs: 13-15. The nucleic acid sequences provided herein are exemplary. One of ordinary skill in the art will recognize that as a result of the degeneracy of the genetic code, whereby more than one codon can encode the same amino acid residue. Tables showing the standard genetic code can be found in various sources (e.g., L. Stryer, 1988, Biochemistry, 3$^{rd}$ Edition, W.H. Freeman and Co., NY).

Nucleic acid molecules encoding a modified Fc-binding domain or nucleic acids encoding a polypeptide including one or more modified Fc-binding domains disclosed herein also include recombinant nucleic acids which are incorporated into a vector, into an autonomously replicating plasmid or virus, or into the genomic DNA of a prokaryote or eukaryote, or which exists as a separate molecule (such as a cDNA) independent of other sequences. A nucleic acid encoding a modified Fc-binding domain or a nucleic acid encoding a polypeptide including one or more modified Fc-binding domains is in some examples operably linked to heterologous expression control sequences. An expression control sequence operably linked to a coding sequence is linked such that expression of the coding sequence is achieved under conditions compatible with the expression control sequences. The expression control sequences include, but are not limited to, promoters, enhancers, transcription terminators, a start codon (e.g., ATG) 5' to a protein-encoding nucleic acid, splicing signal for introns, maintenance of the correct reading frame of that gene to permit proper translation of mRNA, and stop codons. The expression control sequence(s) in some examples are heterologous expression control sequence(s), for example from an organism or species other than the protein-encoding nucleic acid. Thus, the protein-encoding nucleic acid operably linked to a heterologous expression control sequence (such as a promoter) comprises a nucleic acid that is not naturally occurring. In other examples, the nucleic acid is operably linked to a tag sequence (such as 6×His, HA tag, or Myc tag) or another protein-coding sequence, such as a glutathione S-transferase, green fluorescent protein, or maltose binding protein coding sequence.

Vectors for cloning, replication, and/or expression of the disclosed nucleic acid molecules include bacterial plasmids, such as bacterial cloning or expression plasmids (some of which can be used for expression in bacterial and/or mammalian cells). Exemplary bacterial plasmids into which the nucleic acids can be cloned include E. coli plasmids, such as pBR322, pUC plasmids (such as pUC18 or pUC19), pBluescript, pACYC184, pCD1, pGEM® plasmids (such as pGEM®-3, pGEM®-4, pGEM-T® plasmids; Promega, Madison, Wis.), TA-cloning vectors, such as pCR® plasmids (for example, pCR® II, pCR® 2.1, or pCR® 4 plasmids; Life Technologies, Grand Island, N.Y.) or pcDNA plasmids (for example pcDNA™3.1 or pcDNA™3.3 plasmids; Life Technologies). In some examples, the vector includes a heterologous promoter which allows protein expression in bacteria. Exemplary vectors include pET vectors (for example, pET-21b), pDEST™ vectors (Life Technologies), pRSET vectors (Life Technologies), pBAD vectors, and pQE vectors (Qiagen). The disclosed nucleic acids can also be cloned into B. subtilis plasmids, for example, pTA1060 and pHT plasmids (such as pHT01, pHT43, or pHT315 plasmids). Additional vectors suitable for cloning and/or bacterial or mammalian expression of proteins can be selected.

In other embodiments, vectors are used for expression in yeast such as S. cerevisiae or Kluyveromyces lactis. Several promoters are known to be of use in yeast expression systems, such as the constitutive promoters plasma membrane H$^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (20 or single copy (CEN) plasmids to give an additional level of control in expression level. The plasmids can include nutritional markers (such as URA3, ADE3, HIS1, and others) for selection in yeast and antibiotic resistance (such as AMP) for propagation in bacteria. Plasmids for expression on K. lactis are known, such as pKLAC1. Thus, in one example, after amplification in bacteria, plasmids can be introduced into the corresponding yeast auxotrophs by methods similar to bacterial transformation.

DNA sequences encoding a modified Fc-binding domain or encoding a polypeptide including one or more modified Fc-binding domains can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Host cells can include microbial, yeast, insect, or mammalian cells. Methods of expressing DNA sequences having eukaryotic or viral sequences in prokaryotes are well known in the art. Non-limiting examples of suitable host cells include bacteria, Archaea, insect, fungi (for example, yeast), mycobacterium (such as M. smegmatis), plant, and animal cells (for example, mammalian cells, such as human). Exemplary cells of use include E. coli, Bacillus subtilis,

*Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds.), 1979, Cell Culture. *Meth. Enzymol.*, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although other cell lines may be used, such as cells designed to provide higher expression, desirable glycosylation patterns, or other features. As discussed above, techniques for the transformation of yeast cells, such as polyethylene glycol transformation, protoplast transformation and gene guns are also known in the art (see Gietz and Woods *Meth. Enzymol.* 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method. Alternatively, $MgCl_2$ or RbCl can be used. Transformation can also be performed after forming a protoplast of the host cell if desired, or by electroporation.

When the host is a eukaryote, methods of transfection of DNA such as calcium phosphate coprecipitation, mechanical procedures such as microinjection, electroporation, insertion of a plasmid encased in liposomes, or virus vectors can be used. Eukaryotic cells can also be co-transformed with a polynucleotide encoding a protein increasing β cell number (or a portion or fragment thereof) and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Recombinant protein produced by expression in a bacterial, yeast, viral, or mammalian system can be purified. In particular examples, the disclosed modified Fc-binding domains or polypeptides including one or more of the modified Fc-binding domains can be purified using an affinity column including Fc regions (such as an antibody or fragment thereof).

In additional examples, the disclosed modified Fc-binding domains or polypeptides including the modified Fc-binding domains are detectably labeled. Exemplary detectable labels include radioisotopes, fluorophores, haptens, fluorescent proteins, and so on.

III. Methods of Use

Also disclosed herein are methods for purifying polypeptides including one or more Fc regions (such as an antibody or a fragment thereof). In some examples, the method includes contacting a modified Fc-binding domain or a polypeptide including one or more modified Fc-binding domains disclosed herein with a polypeptide including one or more Fc regions at a pH of about 6 or less (such as about pH 5 to pH 6, for example, pH 5, 5.1, 5.2, 5.3, 5.4, 5.5, 5.6, 5.7, 5.8, 5.9, or 6), to form a complex of the modified Fc-binding domain or polypeptide including one or more modified Fc-binding domains and the polypeptide including one or more Fc regions. The polypeptide including one or more Fc regions is subsequently dissociated from the complex by contacting the complex with a buffer above about pH 7 (such as about pH 7 to pH 8.5, for example, pH 7, 7.1, 7.2, 7.3, 7.4, 7.5, 7.6, 7.7, 7.8, 7.9, 8, 8.1, 8.2, 8.3, 8.4, or 8.5). In some examples, the modified Fc-binding domain or polypeptide including one or more modified Fc-binding domains is contacted with the polypeptide including one or more Fc regions in a solution (e.g., a buffer) at pH of about 5.6 and the complex is dissociated with a buffer of about pH 8.2.

In some examples, the modified Fc-binding domain or polypeptide including one or more modified Fc-binding domains is linked to a solid support (such as a surface, bead, or column) and the solid support is contacted with one or more polypeptides including one or more Fc regions (such as a mixture of proteins and/or other components) at a pH below about 6. The polypeptides including one or more Fc regions are eluted from the solid substrate with a buffer having a pH above about 6. In one example, the elution buffer has about pH 8.2. The solid support is optionally washed to remove unbound or non-specifically bound components prior to elution. The pH-dependent affinity of the modified Fc-binding domains or polypeptides including one or more modified Fc-binding domains disclosed herewith permits purification of polypeptides including one or more Fc regions without the use of harsh purification or assay conditions. Therefore, in some embodiments, the purification method does not include detergents, high acidity (e.g., low pH), and/or high salt concentrations.

IV. Reagents and Kits

Also provided are reagents and kits including the modified Fc-binding domains or polypeptides including the modified Fc-binding domains disclosed herein. In some embodiments, a modified Fc-binding domain or a polypeptide including one or more modified Fc-binding domains is linked or conjugated to a solid support.

Examples of solid supports include natural polymeric carbohydrates and their synthetically modified, cross-linked or substituted derivatives, such as agar, agarose, sepharose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

In particular examples, the modified Fc-binding domain or polypeptide including one or more modified Fc-binding domains is linked or conjugated to sepharose, agarose, or polyacrylamide. The modified Fc-binding domain or a polypeptide including one or more modified Fc-binding domains is linked or conjugated to a solid support may be in the form of a column, such as an affinity purification column.

In other embodiments, a kit is provided that includes a modified Fc-binding domain or a polypeptide including one or more modified Fc-binding domains linked or conjugated to a solid support (such as a column including the modified Fc-binding domain or a polypeptide including one or more modified Fc-binding domains linked or conjugated to a solid support) and one or more buffers, such as elution buffer having about pH 7-8.5 (such as about pH 8.2).

EXAMPLES

The following examples are provided to illustrate certain particular features and/or embodiments. These examples should not be construed to limit the disclosure to the particular features or embodiments described.

Example 1

Modified Protein G Polypeptides

Protein G (PrG) binds immunoglobulin G (IgG) at its constant Fc region. Protein G is a common protein used to purify antibodies from a mixture of cellular components. The common purification techniques involve loading the mixture (such as a cell slurry) onto a PrG bound column at pH 7.0 and eluting the antibody using an elution buffer at pH 2.7. This pH is below the pKa of glutamic acid and aspartic acid, polar amino acids that form many salt bridges in proteins for stability. Eluting at this "harsh" pH is potentially detrimental to both PrG and antibody folding and stability. Current efforts in PrG design described below are directed to creating a purification technique that uses elution buffers closer to physiological pH (FIG. 1).

A high performance version of Protein G was previously developed, namely the ERH Protein G variant (Jha et al., *Protein Engineering Design & Selection* 27:127-134, 2014; incorporated by reference in its entirety), but it binds IgG so tightly that it would require rough treatment to elute the antibody after it is bound. Variants have now been developed that can be switched at will, for example, for binding and releasing a target (e.g., an antibody).

All PrG variants were displayed on yeast cell surface. The C2 binding domain gene from Streptococcal PrG (PrG-WT) was synthesized by Genscript with the codon usage optimized for yeast expression (*Saccharomyces cerevisiae* strain). A secretion tag to promote display was placed at the N-terminal and the strand 11 tag from split green fluorescent protein (GFP) (Cabantous et al., *Nature Biotechnology* 23:102-107, 2005) was added to the C-terminal to allow quantitative normalization of the display of full-length PrG. The mutant ERH (PrG-ERH (named for the three altered amino acids)) was generated using two oligos and the Phusion site-directed mutagenesis kit (Thermo Scientific). The mutant PrG-EHH was made using PrG-ERH as template for overlap extension PCR (Horton et al., *Biotechniques* 8:528-535, 1990) using appropriate primers. Similarly, PrG-EHHE and PrG-EHHD were made using PrG-EHH as a template for overlap extension PCR. All five genes were subcloned into pDNL6-GFP11 (Ferrara et al., *PLos One* 6:e25727, 2011), transformed into EBY100 yeast strain following the Yeast transformation kit protocol (Sigma) and verified by sequencing. Growing conditions and strands. 1-10 GFP complementation assays were performed as previously described (Ferrara et al., *PLos One* 6:e25727, 2011).

For binding of IgG to yeast surface-displayed PrG variants, citrate-phosphate buffer (10-25 mM, pH5.6, 100-140 mM NaCl), phosphate buffered saline (pH 7.4), sodium phosphate buffer (10-25 mM, pH 7.2-7.4, 100-140 mM NaCl) and Tris-HCl buffer (6-25 mM, pH 8.2, 100-140 mM NaCl) were used in different set of experiments. In a suitable buffer, yeast cells were incubated with different concentrations of AlexaFluor 647-conjugated human IgG (Jackson Immuno Research) with gentle shaking for up to 30 mins. The molecular affinities (dissociation constant or $K_d$) of wild-type (PrG-WT), mutant (PrG-EHHE) and PrG-EHHD towards IgG were calculated directly on the yeast surface by fitting the display-normalized fluorescence of serial titrations of fluorescently labeled antibody (Chao et al., *Nature Protocols* 1:755-768, 2006) to yeast cells displaying the different PrG forms. This method of calculating affinity (Boder and Wittrup, *Methods in Enzymology* 328:430-444, 2000) shows consistency with other techniques (Gal and Wittrup, *Current Opinion in Structural Biology* 17:467-473, 2007). The AlexaFluor 647-conjugated human IgG, was determined to have no fluorescent crosstalk with the GFP, allowing two-channel flow cytometer assays to separately measure display and antibody capture.

Figure 2A:
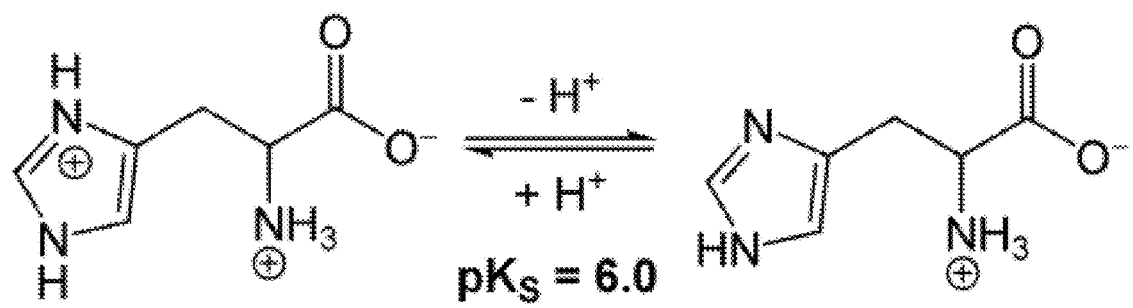
FIG. 2A is a schematic showing the charge switch in histidine at pH 6.0 (the pKa of histidine).
Figure 2B:
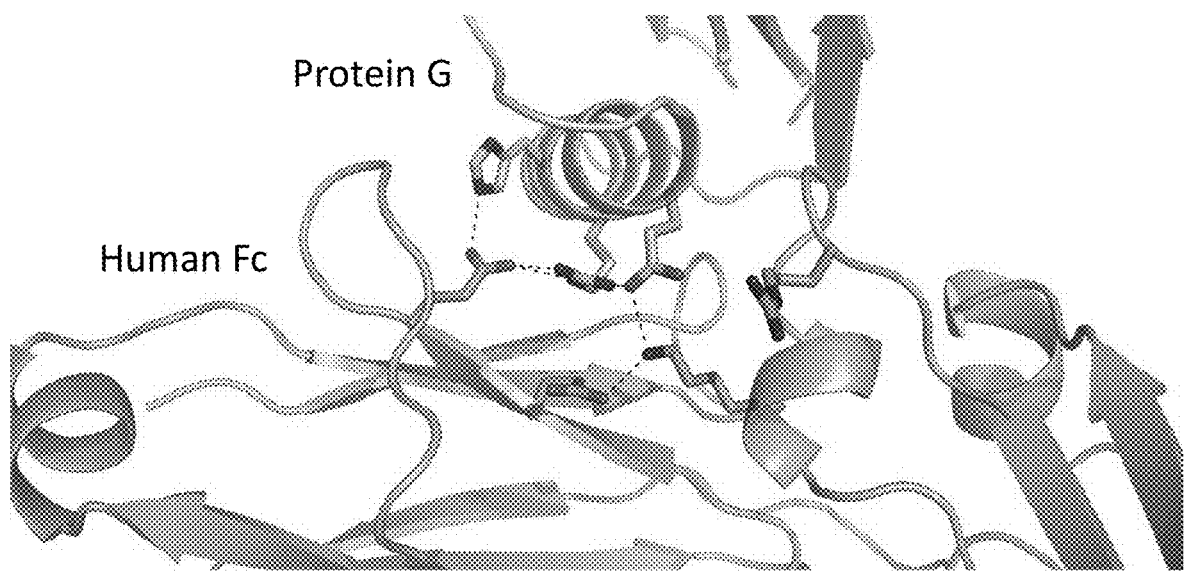
FIG. 2B is a ribbon drawing showing human Fc bound to ERH mutant Protein G (PrG). Histidines added to the rim of the binding site of PrG change the charge of the pocket.

The modified polypeptides included Protein G with A24E, K28R, and V29H in the C2 domain (ERH), A24E, K28H, and V29H in the C2 domain (EHH); A24E, K28H, V29H, and N35E in the C2 domain (EHHE); and A24E, K28H, V29H, and N35D in the C2 domain (EHHD). The amino acid histidine has a pKa of roughly 6.0, where a "charge switch" occurs (FIG. 2A). Histidines added to the rim of the binding site of Protein G can change the charge of the pocket (FIG. 2B).

Figure 3:
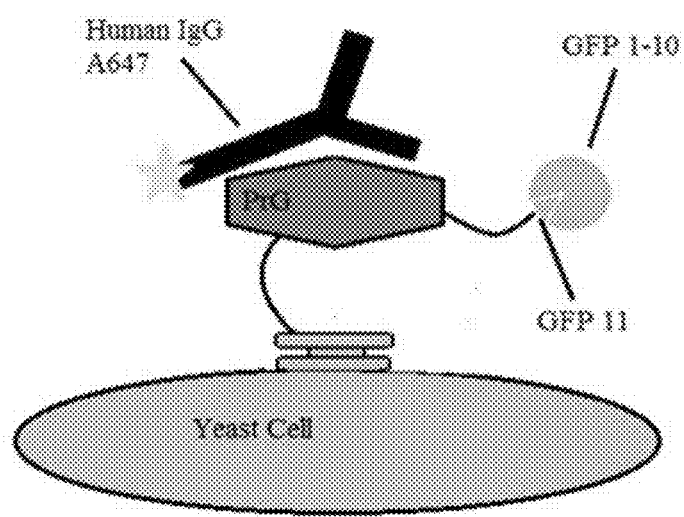
FIG. 3 is a schematic diagram showing the method utilized to screen Protein G mutants. Protein G (PrG) is displayed on the surface of yeast cells and binds to the Fc stalk region of a fluorescently labeled human IgG antibody. The Protein G has a C-terminal strand 11 tag, which complements exogenous split GFP (strand 1-10), providing an independent mechanism to monitor display of the Protein G. Affinity and display levels can be measured by flow cytometry.
Figure 4:
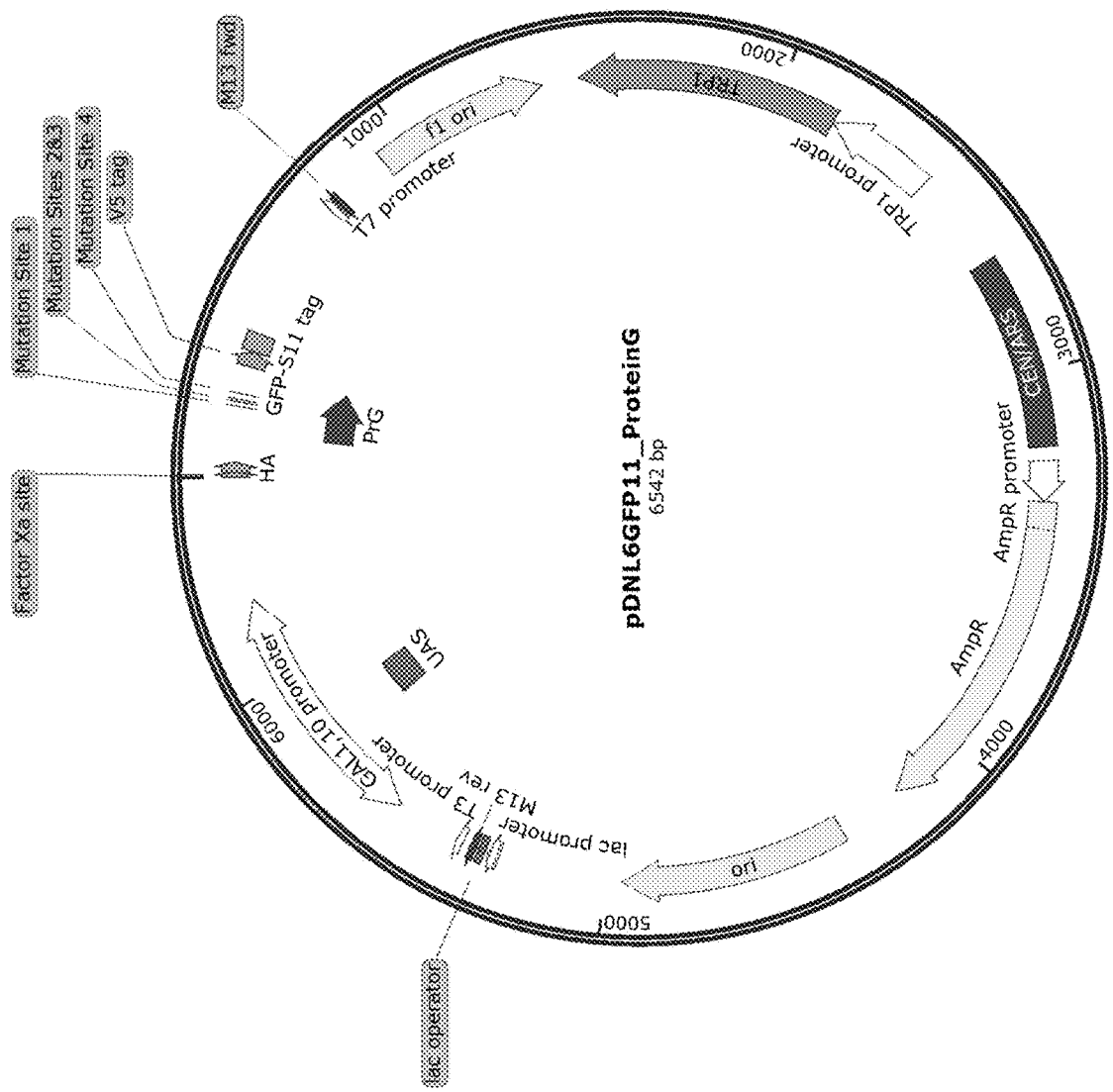
FIG. 4 is a vector map of an exemplary plasmid used to display Protein G on yeast cells.

Modified Protein G polypeptides were cloned into a yeast-compatible plasmid (FIG. 4), transformed into yeast host cells, and displayed on the yeast cell surface (FIG. 3). The Protein G polypeptides also included a secretion tag at the N-terminus to promote surface display and the strand 11 tag from split green fluorescent protein (GFP, strand 1-10) at the C-terminus to allow quantitation of the display level of the Protein G (FIG. 3). Human IgG labeled with AlexaFlour 647 was used as the binding substrate for the Protein G and flow cytometry was used to detect IgG binding and Protein G display.

Figure 5:
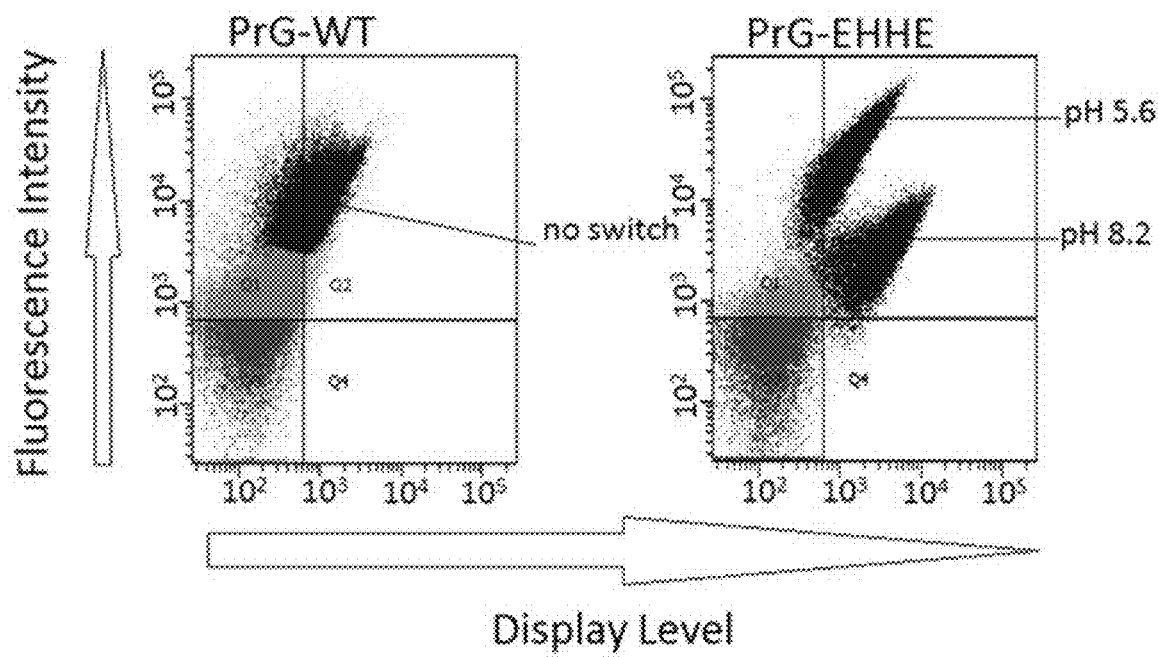
FIG. 5 is a pair of flow cytometry 2D-dot plots showing affinity of WT protein G (left) and PrG-EHHE (right) for IgG at pH 5.6 and pH 8.2.
Figure 6:
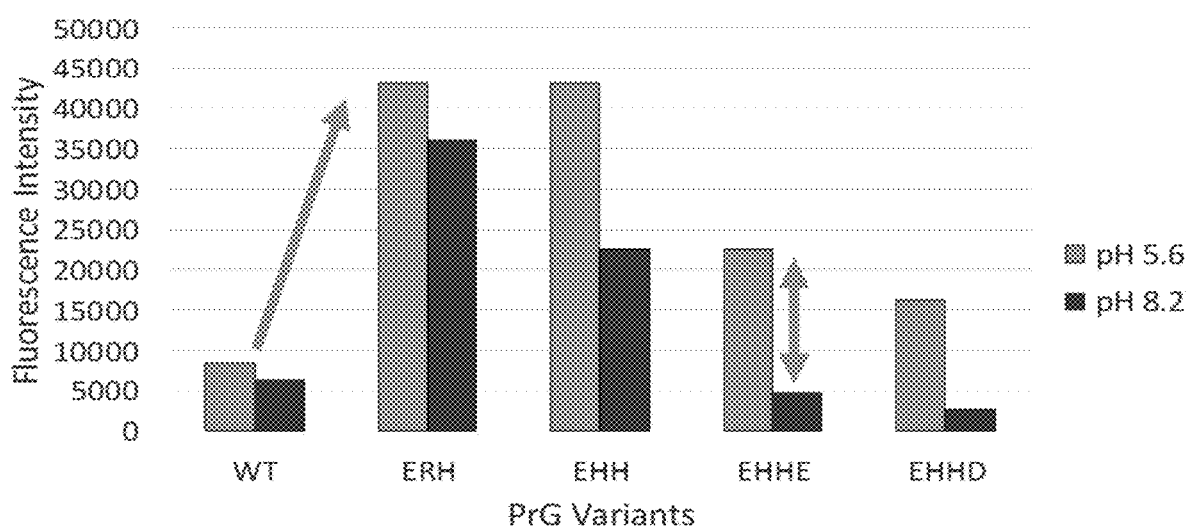
FIG. 6 is a graph qualitatively showing affinity of WT PrG and the indicated PrG variants at pH 5.6 and pH 8.2. With the addition of charged side groups, like arginine and/or histidine, the IgG binding affinity increased by a few-fold (first arrow; ERH and EHH). Some affinity was lost with the addition of a glutamic acid (EHHE), but the pH-dependent affinity switch showed improvement (second arrow).

The affinity of EHHE Protein G for IgG showed pH dependence, with higher affinity at pH 5.6 and decreased affinity at pH 8.2 (FIG. 5). Addition of charged amino acids, especially histidine, increased the IgG binding affinity by at least 4-fold for ERH and EHH Protein G (FIG. 6). Some affinity was lost with the addition of a glutamic acid (EHHE), but the EHHE still had increased affinity for IgG compared to wild type, and the pH dependent switch increased by at least 2-fold (FIG. 6). The change from asparagine to aspartic acid (EHHD), although closer sterically to the native Protein G, did not lend a better switch or better binding than EHHE (FIG. 6).

Figure 7A:
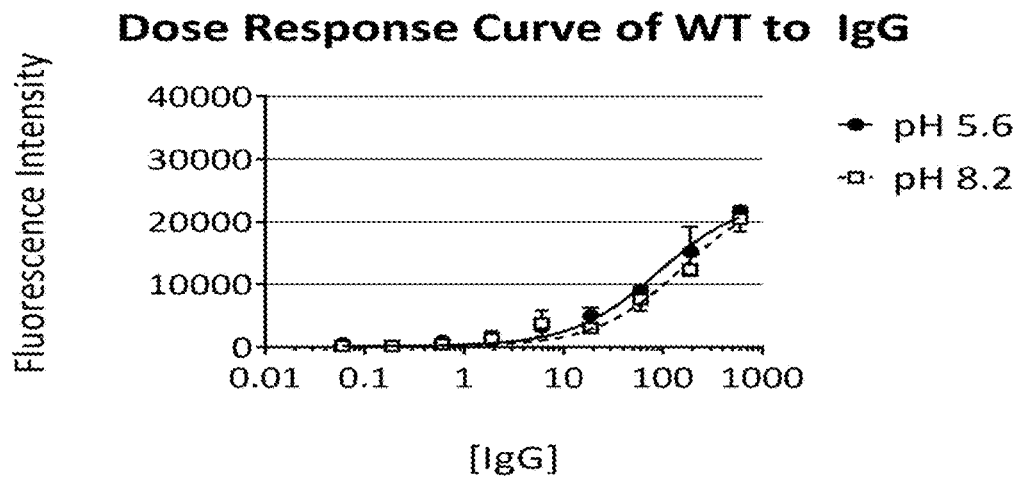
FIGS. 7A-7C are a series of graphs showing dose response curves of PrG to IgG at pH 5.6 and pH 8.2 for WT PrG (FIG. 7A) and EHHE (FIG. 7B) and EHHD (FIG. 7B) variants of PrG.
Figure 7B:
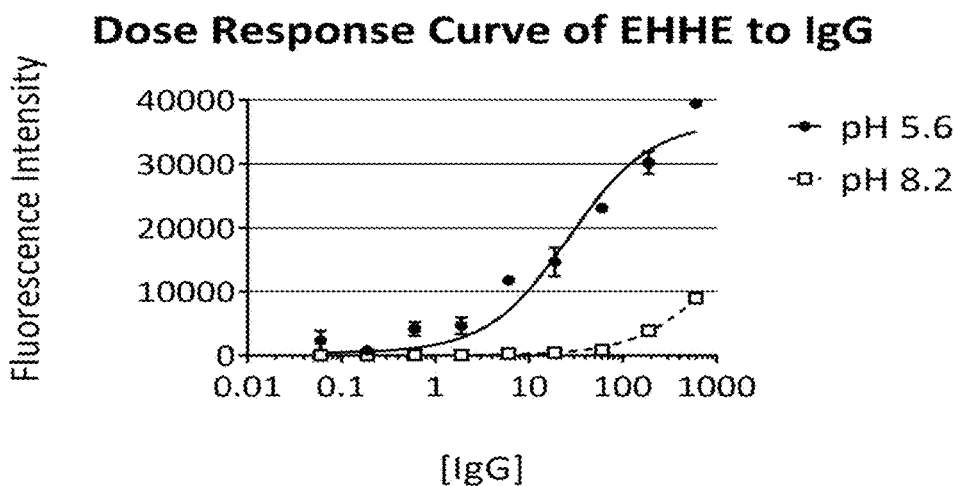
Figure 7C:
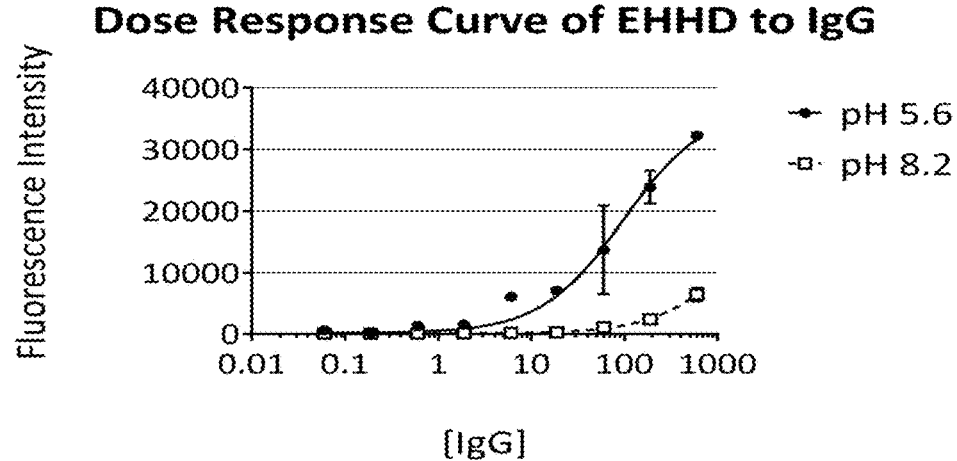

Dose response of EHHE, EHHD, and wild type Protein G to IgG are shown in FIGS. 7A-7C. The binding constant that determines concentration of IgG at which 50% Protein G molecules are in bound state increased when pH was switched from 5.6 to 8.2. WT PrG showed marginal change in binding constant (<2-fold) while the PrG variants EHHE and EHHD showed a dramatic change in binding constant (40- and 20-fold respectively) (Table 1).

TABLE 1

Measured binding constant values for wild type (WT) and modified Protein G against human IgG

| | pH | |
|---|---|---|
| | 5.6 | 8.2 |
| WT | 92 nM | 158 nM |
| EHHE | 27 nM | 1172 nM |
| EHHD | 96 nM | 1785 nM |

Figure 8A:
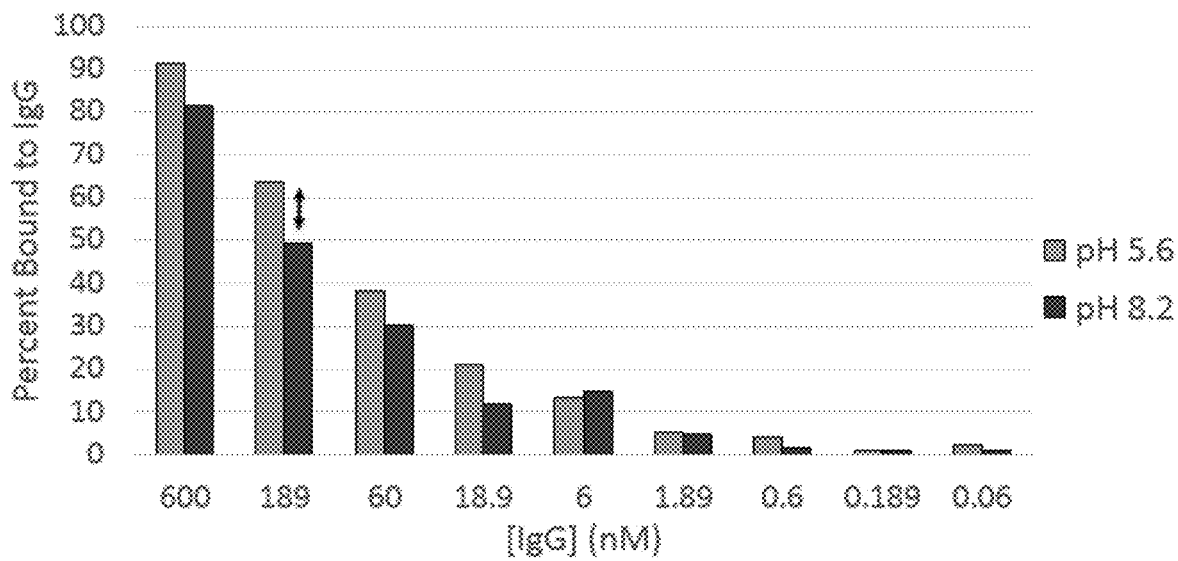
FIGS. 8A-8C are a series of graphs showing percent binding of PrG to the indicated concentrations of IgG at pH 5.6 and pH 8.2 for WT (FIG. 8A), EHHE (FIG. 8B), and EHHD (FIG. 8C) PrG. Arrows illustrate the pH dependent switch in binding affinity.
Figure 8B:
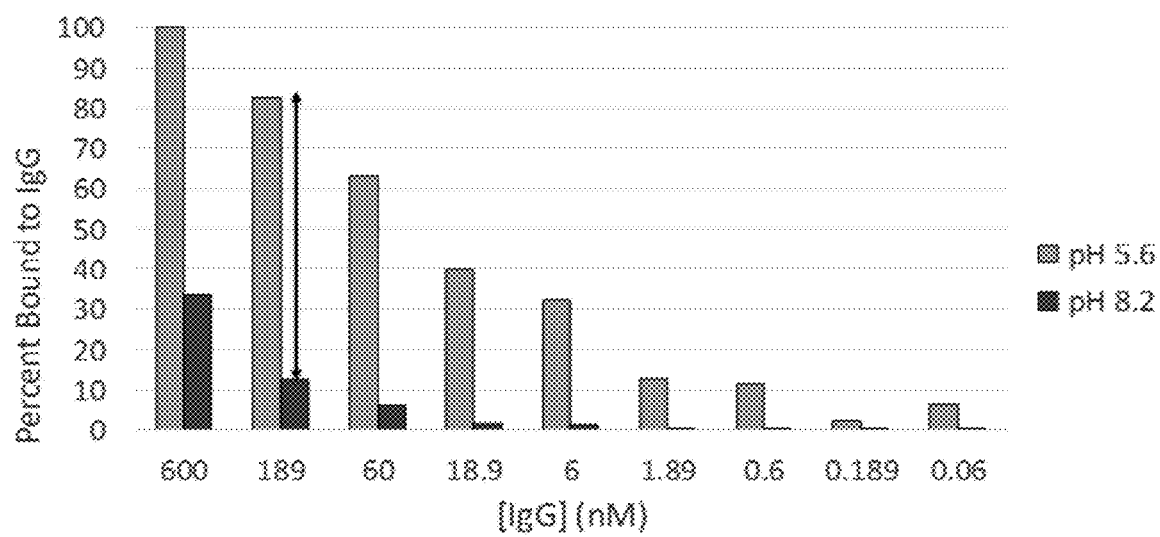
Figure 8C:
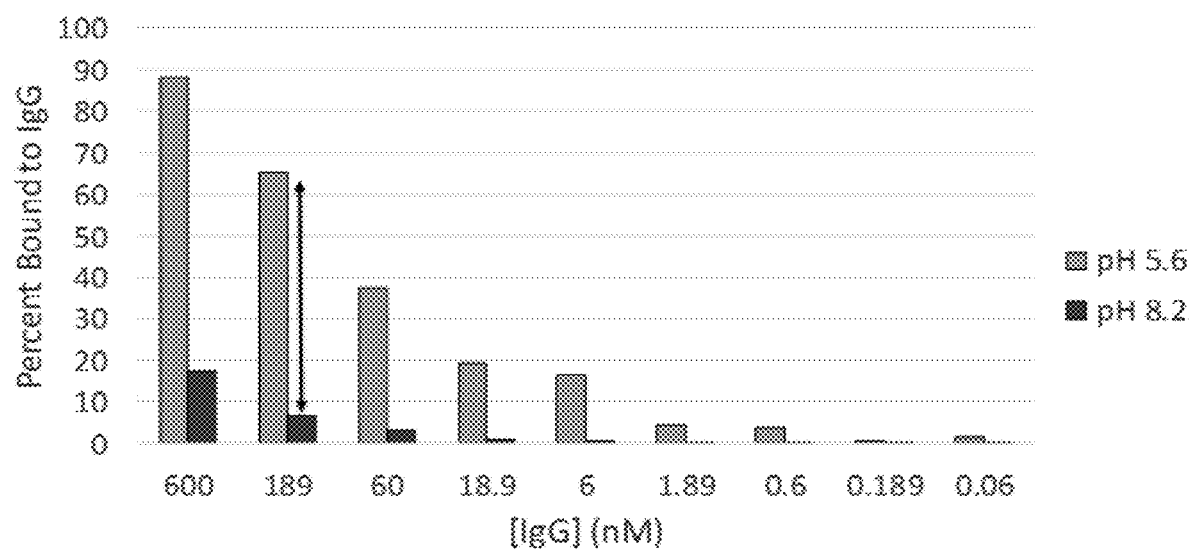
Figure 9:
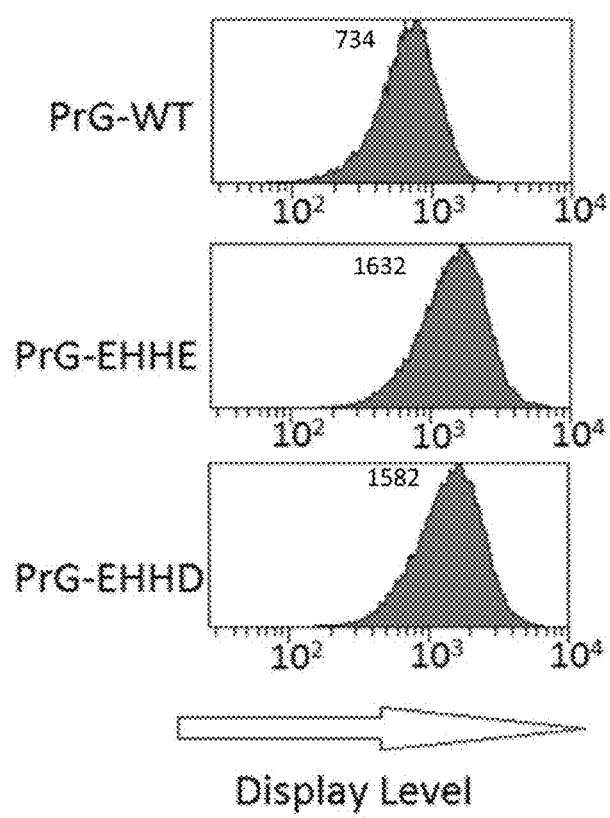
FIG. 9 is a series of histograms of PrG display for WT (top), EHHE (middle), and EHHD (bottom) at pH 5.6. Both mutants have improved PrG display compared to WT.

The pH-dependent switch for EHHE and EHHD compared to wild type Protein G is clearly seen in FIGS. 8A-8C. The percentage of bound IgG at an IgG concentration of approximately 200 nM (which provides the greatest pH switch) is shown in Table 2. Both EHHE and EHHD had improved display in yeast cells compared to wild type Protein G (FIG. 9).

TABLE 2

Percent IgG bound to PrG variants at IgG concentration of ~200 nM

| | pH | |
|---|---|---|
| | 5.6 | 8.2 |
| WT | 65 | 50 |
| EHHE | 80 | 10 |
| EHHD | 65 | 7 |

Example 2

Efficiency of Binding and Elution of IgG to Variant Protein G

Protein G variants described in Example 1 are purified as His-tagged proteins, and immobilized on a HiTrap-NHS activated HP column (GE Healthcare sciences) according to manufacturer's protocol such that the bound PrG is greater than 1 μM in the column. Purified IgG (for example human IgG 14506 or 12511 from Sigma-Aldrich) or serum containing IgG (Serum H5667 from Sigma-Aldrich) in a buffer at pH 5.6 are loaded on the column equilibrated at the same pH. A typical IgG concentration of 30 μg/ml equivalent to ~200 nM of IgG is used for both purified and serum versions of the load. Post binding, the column is thoroughly washed with greater than 5 column volumes of the pH 5.6 buffer. An elution buffer at pH 8.2 is used to elute the bound protein. Typically two column volumes of buffer are used to fully retrieve the bound IgG from the column. The percentage of IgG bound to the column is calculated based on the amount applied to the column and the amount in the flow-through. The percentage of IgG eluted is calculated based on the amount of IgG bound to the column and the amount eluted from the column. Finally, the purification efficiency is calculated as (IgG Quantity in Eluate)/(IgG Quantity in Load) × 100.

Since Hi-Trap NHS activated column binds to free amines group in a protein and wild-type Lysine28 is prone to bind to the resin, potentially masking the binding interface, alternatively, a cystine mutation is created at the C-terminus of the PrG (for example E56C) and expressed. The purified PrG variants are then liked to SulfoLink coupling resin (ThermoFisher Scientific). The volume of packed resin column, concentration of IgG in the load, binding and elution conditions are followed as described previously.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

---

We claim:

1. A modified Fc-binding domain polypeptide comprising the amino acid sequence of SEQ ID NO: 4, SEQ ID NO: 6, or SEQ ID NO: 8.

2. The modified Fc-binding domain polypeptide of claim 1, wherein the modified Fc-binding domain consists of the amino acid sequence of SEQ ID NO: 4, SEQ ID NO: 6, or SEQ ID NO: 8.

3. A nucleic acid encoding the modified Fc-binding domain polypeptide of claim 1.

4. The nucleic acid of claim 3, comprising the nucleic acid sequence of any one of SEQ ID NO: 3, SEQ ID NO: 5, or SEQ ID NO: 7.

5. An immunoglobulin-binding protein comprising one or more modified Fc-binding domain polypeptides of claim 1.

6. The immunoglobulin-binding protein of claim 5, comprising the amino acid sequence of any one of SEQ ID NOs: 10-12.

7. A nucleic acid encoding the immunoglobulin-binding protein of claim 5.

8. The nucleic acid of claim 7, comprising the nucleic acid sequence of any one of SEQ ID NOs: 13-15.

9. A vector comprising the nucleic acid of claim 3, operably linked to a promoter.

10. The modified Fc-binding domain polypeptide of claim 1 or an immunoglobulin-binding protein comprising one or more of the modified Fc-binding domain polypeptides, linked to a solid support.

11. The modified Fc-binding domain polypeptide or the immunoglobulin-binding protein linked to a solid support of claim 10, wherein the solid support comprises agarose, sepharose, or polyacrylamide.

12. A kit comprising the modified Fc-binding domain polypeptide or the immunoglobulin-binding protein linked to a solid support of claim 10 and one or more buffers.

13. The kit of claim 12, wherein the one or more buffers comprises an elution buffer with a pH of about 7-8.2.

14. A method of purifying a polypeptide including one or more Fc regions, comprising:
   contacting the modified Fc-binding domain polypeptide of claim 1 or an immunoglobulin-binding protein comprising one or more of the modified Fc-binding domain polypeptides with a polypeptide including one or more Fc regions at a pH of about 6 or less to form a complex of the modified Fc-binding domain or the immunoglobulin-binding protein and the polypeptide including one or more Fc regions; and
   contacting the complex with a buffer above about pH 7 to dissociate the polypeptide including one or more Fc regions.

15. The method of claim 14, wherein the modified Fc-binding domain polypeptide or the immunoglobulin-binding protein is linked to a solid support.

16. The method of claim 14, wherein the modified Fc-binding domain polypeptide or the immunoglobulin-binding protein is contacted with the polypeptide including one or more Fc regions at a pH of about 5.6.

17. The method of claim 14, wherein the buffer above about 6 pH 7 to dissociate the polypeptide including one or more Fc regions comprises a buffer with pH about 8.2.

18. The nucleic acid of claim 4, consisting of the nucleic acid sequence of any one of SEQ ID NO: 3, SEQ ID NO: 5, or SEQ ID NO: 7.

19. The immunoglobulin-binding protein of claim 6, consisting of the amino acid sequence of any one of SEQ ID NOs: 10-12.

20. The nucleic acid of claim 8, consisting of the nucleic acid sequence of any one of SEQ ID NOs: 13-15.

\* \* \* \* \*

SEQUENCE LISTING

<160> NUMBER OF SEQ ID NOS: 15

<210> SEQ ID NO 1
<211> LENGTH: 593
<212> TYPE: PRT
<213> ORGANISM: Streptococcus sp.

<400> SEQUENCE: 1

```
Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Ala Glu Asn Ala Gly Ala Ala Ala Trp Glu
                85                  90                  95

Ala Ala Ala Ala Ala Asp Ala Leu Ala Lys Ala Lys Ala Asp Ala Leu
            100                 105                 110
```

-continued

```
Lys Glu Phe Asn Lys Tyr Gly Val Ser Asp Tyr Tyr Lys Asn Leu Ile
            115                 120                 125
Asn Asn Ala Lys Thr Val Glu Gly Val Lys Asp Leu Gln Ala Gln Val
130                 135                 140
Val Glu Ser Ala Lys Lys Ala Arg Ile Ser Glu Ala Thr Asp Gly Leu
145                 150                 155                 160
Ser Asp Phe Leu Lys Ser Gln Thr Pro Ala Glu Asp Thr Val Lys Ser
                165                 170                 175
Ile Glu Leu Ala Glu Ala Lys Val Leu Ala Asn Arg Glu Leu Asp Lys
            180                 185                 190
Tyr Gly Val Ser Asp Tyr His Lys Asn Leu Ile Asn Asn Ala Lys Thr
        195                 200                 205
Val Glu Gly Val Lys Asp Leu Gln Ala Gln Val Val Glu Ser Ala Lys
    210                 215                 220
Lys Ala Arg Ile Ser Glu Ala Thr Asp Gly Leu Ser Asp Phe Leu Lys
225                 230                 235                 240
Ser Gln Thr Pro Ala Glu Asp Thr Val Lys Ser Ile Glu Leu Ala Glu
                245                 250                 255
Ala Lys Val Leu Ala Asn Arg Glu Leu Asp Lys Tyr Gly Val Ser Asp
            260                 265                 270
Tyr Tyr Lys Asn Leu Ile Asn Asn Ala Lys Thr Val Glu Gly Val Lys
        275                 280                 285
Ala Leu Ile Asp Glu Ile Leu Ala Ala Leu Pro Lys Thr Asp Thr Tyr
    290                 295                 300
Lys Leu Ile Leu Asn Gly Lys Thr Leu Lys Gly Glu Thr Thr Thr Glu
305                 310                 315                 320
Ala Val Asp Ala Ala Thr Ala Glu Lys Val Phe Lys Gln Tyr Ala Asn
                325                 330                 335
Asp Asn Gly Val Asp Gly Glu Trp Thr Tyr Asp Asp Ala Thr Lys Thr
            340                 345                 350
Phe Thr Val Thr Glu Lys Pro Glu Val Ile Asp Ala Ser Glu Leu Thr
        355                 360                 365
Pro Ala Val Thr Thr Tyr Lys Leu Val Ile Asn Gly Lys Thr Leu Lys
    370                 375                 380
Gly Glu Thr Thr Thr Glu Ala Val Asp Ala Ala Thr Ala Glu Lys Val
385                 390                 395                 400
Phe Lys Gln Tyr Ala Asn Asp Asn Gly Val Asp Gly Glu Trp Thr Tyr
                405                 410                 415
Asp Asp Ala Thr Lys Thr Phe Thr Val Thr Glu Lys Pro Glu Val Ile
            420                 425                 430
Asp Ala Ser Glu Leu Thr Pro Ala Val Thr Thr Tyr Lys Leu Val Ile
        435                 440                 445
Asn Gly Lys Thr Leu Lys Gly Glu Thr Thr Thr Lys Ala Val Asp Ala
    450                 455                 460
Glu Thr Ala Glu Lys Ala Phe Lys Gln Tyr Ala Asn Asp Asn Gly Val
465                 470                 475                 480
Asp Gly Val Trp Thr Tyr Asp Asp Ala Thr Lys Thr Phe Thr Val Thr
                485                 490                 495
Glu Met Val Thr Glu Val Pro Gly Asp Ala Pro Thr Glu Pro Glu Lys
            500                 505                 510
Pro Glu Ala Ser Ile Pro Leu Val Pro Leu Thr Pro Ala Thr Pro Ile
        515                 520                 525
Ala Lys Asp Asp Ala Lys Lys Asp Asp Thr Lys Lys Glu Asp Ala Lys
```

```
                530             535             540
Lys Pro Glu Ala Lys Lys Glu Asp Ala Lys Lys Ala Glu Thr Leu Pro
545                 550                 555                 560

Thr Thr Gly Glu Gly Ser Asn Pro Phe Phe Thr Ala Ala Ala Leu Ala
                565                 570                 575

Val Met Ala Gly Ala Gly Ala Leu Ala Val Ala Ser Lys Arg Lys Glu
                580                 585                 590

Asp

<210> SEQ ID NO 2
<211> LENGTH: 56
<212> TYPE: PRT
<213> ORGANISM: Artificial Sequence
<220> FEATURE:
<223> OTHER INFORMATION: Protein G C2 domain

<400> SEQUENCE: 2

Thr Thr Tyr Lys Leu Val Ile Asn Gly Lys Thr Leu Lys Gly Glu Thr
1               5                   10                  15

Thr Thr Glu Ala Val Asp Ala Ala Thr Ala Glu Lys Val Phe Lys Gln
                20                  25                  30

Tyr Ala Asn Asp Asn Gly Val Asp Gly Glu Trp Thr Tyr Asp Asp Ala
            35                  40                  45

Thr Lys Thr Phe Thr Val Thr Glu
        50                  55

<210> SEQ ID NO 3
<211> LENGTH: 168
<212> TYPE: DNA
<213> ORGANISM: Artificial Sequence
<220> FEATURE:
<223> OTHER INFORMATION: Protein G EHH C2 domain encoding sequence

<400> SEQUENCE: 3
acaacctata aattagtcat aaacggtaaa acattgaagg gtgaaaccac aactgaagct      60
gtagacgccg aaactgctga acaccatttt aaacaatatg ctaatgataa tggtgtagat     120
ggtgaatgga cctatgatga cgccactaag acctttactg ttactgaa                  168

<210> SEQ ID NO 4
<211> LENGTH: 56
<212> TYPE: PRT
<213> ORGANISM: Artificial Sequence
<220> FEATURE:
<223> OTHER INFORMATION: Protein G EHH C2 domain

<400> SEQUENCE: 4

Thr Thr Tyr Lys Leu Val Ile Asn Gly Lys Thr Leu Lys Gly Glu Thr
1               5                   10                  15

Thr Thr Glu Ala Val Asp Ala Glu Thr Ala Glu His His Phe Lys Gln
                20                  25                  30

Tyr Ala Asn Asp Asn Gly Val Asp Gly Glu Trp Thr Tyr Asp Asp Ala
            35                  40                  45

Thr Lys Thr Phe Thr Val Thr Glu
        50                  55

<210> SEQ ID NO 5
<211> LENGTH: 168
<212> TYPE: DNA
<213> ORGANISM: Artificial Sequence
<220> FEATURE:
```

<223> OTHER INFORMATION: Protein G EHHE C2 domain encoding sequence

<400> SEQUENCE: 5
acaacctata aattagtcat aaacggtaaa acattgaagg gtgaaaccac aactgaagct 60
gtagacgccg aaactgctga acaccatttt aaacaatatg ctgaagataa tggtgtagat 120
ggtgaatgga cctatgatga cgccactaag acctttactg ttactgaa 168

<210> SEQ ID NO 6
<211> LENGTH: 56
<212> TYPE: PRT
<213> ORGANISM: Artificial Sequence
<220> FEATURE:
<223> OTHER INFORMATION: Protein G EHHE C2 domain

<400> SEQUENCE: 6

Thr Thr Tyr Lys Leu Val Ile Asn Gly Lys Thr Leu Lys Gly Glu Thr
1               5                   10                  15

Thr Thr Glu Ala Val Asp Ala Glu Thr Ala Glu His His Phe Lys Gln
            20                  25                  30

Tyr Ala Glu Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 7
<211> LENGTH: 168
<212> TYPE: DNA
<213> ORGANISM: Artificial Sequence
<220> FEATURE:
<223> OTHER INFORMATION: Protein G EHHD C2 domain encoding sequence

<400> SEQUENCE: 7
acaacctata aattagtcat aaacggtaaa acattgaagg gtgaaaccac aactgaagct 60
gtagacgccg aaactgctga acaccatttt aaacaatatg ctgacgataa tggtgtagat 120
ggtgaatgga cctatgatga cgccactaaa acctttactg ttactgaa 168

<210> SEQ ID NO 8
<211> LENGTH: 56
<212> TYPE: PRT
<213> ORGANISM: Artificial Sequence
<220> FEATURE:
<223> OTHER INFORMATION: Protein G EHHD C2 domain

<400> SEQUENCE: 8

Thr Thr Tyr Lys Leu Val Ile Asn Gly Lys Thr Leu Lys Gly Glu Thr
1               5                   10                  15

Thr Thr Glu Ala Val Asp Ala Glu Thr Ala Glu His His Phe Lys Gln
            20                  25                  30

Tyr Ala Asp Asp Asn Gly Val Asp Gly Glu Trp Thr Tyr Asp Asp Ala
        35                  40                  45

Thr Lys Thr Phe Thr Val Thr Glu
    50                  55

<210> SEQ ID NO 9
<211> LENGTH: 56
<212> TYPE: PRT
<213> ORGANISM: Artificial Sequence
<220> FEATURE:
<223> OTHER INFORMATION: Protein G ERH C2 domain

<400> SEQUENCE: 9

```
Thr Thr Tyr Lys Leu Val Ile Asn Gly Lys Thr Leu Lys Gly Glu Thr
1               5                   10                  15

Thr Thr Glu Ala Val Asp Ala Glu Thr Ala Glu Arg His Phe Lys Gln
            20                  25                  30

Tyr Ala Asn Asp Asn Gly Val Asp Gly Glu Trp Thr Tyr Asp Asp Ala
            35                  40                  45

Thr Lys Thr Phe Thr Val Thr Glu
        50                  55

<210> SEQ ID NO 10
<211> LENGTH: 593
<212> TYPE: PRT
<213> ORGANISM: Artificial Sequence
<220> FEATURE:
<223> OTHER INFORMATION: Protein G EHH variant

<400> SEQUENCE: 10

Met Glu Lys Glu Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
            35                  40                  45

Glu Leu Thr Asn Leu Leu Gly Asn Ser Glu Thr Thr Leu Ala Leu Arg
50                  55                  60

Asn Glu Glu Ser Ala Thr Ala Asp Leu Thr Ala Ala Ala Val Ala Asp
65                  70                  75                  80

Thr Val Ala Ala Ala Ala Glu Asn Ala Gly Ala Ala Ala Trp Glu
            85                  90                  95

Ala Ala Ala Ala Asp Ala Leu Ala Lys Ala Lys Ala Asp Ala Leu
            100                 105                 110

Lys Glu Phe Asn Lys Tyr Gly Val Ser Asp Tyr Tyr Lys Asn Leu Ile
            115                 120                 125

Asn Asn Ala Lys Thr Val Glu Gly Val Lys Asp Leu Gln Ala Gln Val
130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
            165                 170                 175

Ile Glu Leu Ala Glu Ala Lys Val Leu Ala Asn Arg Glu Leu Asp Lys
            180                 185                 190

Tyr Gly Val Ser Asp Tyr His Lys Asn Leu Ile Asn Asn Ala Lys Thr
            195                 200                 205

Val Glu Gly Val Lys Asp Leu Gln Ala Gln Val Val Glu Ser Ala Lys
            210                 215                 220

Lys Ala Arg Ile Ser Glu Ala Thr Asp Gly Leu Ser Asp Phe Leu Lys
225                 230                 235                 240

Ser Gln Thr Pro Ala Glu Asp Thr Val Lys Ser Ile Glu Leu Ala Glu
            245                 250                 255

Ala Lys Val Leu Ala Asn Arg Glu Leu Asp Lys Tyr Gly Val Ser Asp
            260                 265                 270

Tyr Tyr Lys Asn Leu Ile Asn Asn Ala Lys Thr Val Glu Gly Val Lys
            275                 280                 285

Ala Leu Ile Asp Glu Ile Leu Ala Ala Leu Pro Lys Thr Asp Thr Tyr
            290                 295                 300
```

-continued

```
Lys Leu Ile Leu Asn Gly Lys Thr Leu Lys Gly Glu Thr Thr Thr Glu
305                 310                 315                 320

Ala Val Asp Ala Glu Thr Ala Glu His His Phe Lys Gln Tyr Ala Asn
            325                 330                 335

Asp Asn Gly Val Asp Gly Glu Trp Thr Tyr Asp Asp Ala Thr Lys Thr
        340                 345                 350

Phe Thr Val Thr Glu Lys Pro Glu Val Ile Asp Ala Ser Glu Leu Thr
    355                 360                 365

Pro Ala Val Thr Thr Tyr Lys Leu Val Ile Asn Gly Lys Thr Leu Lys
370                 375                 380

Gly Glu Thr Thr Thr Glu Ala Val Asp Ala Thr Ala Glu His His
385                 390                 395                 400

Phe Lys Gln Tyr Ala Asn Asp Asn Gly Val Asp Gly Glu Trp Thr Tyr
            405                 410                 415

Asp Asp Ala Thr Lys Thr Phe Thr Val Thr Glu Lys Pro Glu Val Ile
        420                 425                 430

Asp Ala Ser Glu Leu Thr Pro Ala Val Thr Thr Tyr Lys Leu Val Ile
    435                 440                 445

Asn Gly Lys Thr Leu Lys Gly Glu Thr Thr Thr Lys Ala Val Asp Ala
450                 455                 460

Glu Thr Ala Glu His His Phe Lys Gln Tyr Ala Asn Asp Asn Gly Val
465                 470                 475                 480

Asp Gly Val Trp Thr Tyr Asp Asp Ala Thr Lys Thr Phe Thr Val Thr
            485                 490                 495

Glu Met Val Thr Glu Val Pro Gly Asp Ala Pro Thr Glu Pro Glu Lys
        500                 505                 510

Pro Glu Ala Ser Ile Pro Leu Val Pro Leu Thr Pro Ala Thr Pro Ile
    515                 520                 525

Ala Lys Asp Asp Ala Lys Lys Asp Asp Thr Lys Lys Glu Asp Ala Lys
530                 535                 540

Lys Pro Glu Ala Lys Lys Glu Asp Ala Lys Lys Ala Glu Thr Leu Pro
545                 550                 555                 560

Thr Thr Gly Glu Gly Ser Asn Pro Phe Phe Thr Ala Ala Ala Leu Ala
            565                 570                 575

Val Met Ala Gly Ala Gly Ala Leu Ala Val Ala Ser Lys Arg Lys Glu
        580                 585                 590

Asp
```

<210> SEQ ID NO 11
<211> LENGTH: 593
<212> TYPE: PRT
<213> ORGANISM: Artificial Sequence
<220> FEATURE:
<223> OTHER INFORMATION: Protein G EHHE variant

<400> SEQUENCE: 11

```
Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60
```

```
Asn Glu Glu Ser Ala Thr Ala Asp Leu Thr Ala Ala Val Ala Asp
 65                  70                  75                  80

Thr Val Ala Ala Ala Ala Glu Asn Ala Gly Ala Ala Ala Trp Glu
                 85                  90                  95

Ala Ala Ala Ala Ala Asp Ala Leu Ala Lys Ala Lys Ala Asp Ala Leu
                100                 105                 110

Lys Glu Phe Asn Lys Tyr Gly Val Ser Asp Tyr Tyr Lys Asn Leu Ile
            115                 120                 125

Asn Asn Ala Lys Thr Val Glu Gly Val Lys Asp Leu Gln Ala Gln Val
            130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
                180                 185                 190

Tyr Gly Val Ser Asp Tyr His Lys Asn Leu Ile Asn Asn Ala Lys Thr
            195                 200                 205

Val Glu Gly Val Lys Asp Leu Gln Ala Gln Val Val Glu Ser Ala Lys
210                 215                 220

Lys Ala Arg Ile Ser Glu Ala Thr Asp Gly Leu Ser Asp Phe Leu Lys
225                 230                 235                 240

Ser Gln Thr Pro Ala Glu Asp Thr Val Lys Ser Ile Glu Leu Ala Glu
                245                 250                 255

Ala Lys Val Leu Ala Asn Arg Glu Leu Asp Lys Tyr Gly Val Ser Asp
                260                 265                 270

Tyr Tyr Lys Asn Leu Ile Asn Asn Ala Lys Thr Val Glu Gly Val Lys
            275                 280                 285

Ala Leu Ile Asp Glu Ile Leu Ala Ala Leu Pro Lys Thr Asp Thr Tyr
            290                 295                 300

Lys Leu Ile Leu Asn Gly Lys Thr Leu Lys Gly Glu Thr Thr Thr Glu
305                 310                 315                 320

Ala Val Asp Ala Glu Thr Ala Glu His His Phe Lys Gln Tyr Ala Glu
                325                 330                 335

Asp Asn Gly Val Asp Gly Glu Trp Thr Tyr Asp Asp Ala Thr Lys Thr
            340                 345                 350

Phe Thr Val Thr Glu Lys Pro Glu Val Ile Asp Ala Ser Glu Leu Thr
            355                 360                 365

Pro Ala Val Thr Thr Tyr Lys Leu Val Ile Asn Gly Lys Thr Leu Lys
            370                 375                 380

Gly Glu Thr Thr Thr Glu Ala Val Asp Ala Glu Thr Ala Glu His His
385                 390                 395                 400

Phe Lys Gln Tyr Ala Glu Asp Asn Gly Val Asp Gly Glu Trp Thr Tyr
                405                 410                 415

Asp Asp Ala Thr Lys Thr Phe Thr Val Thr Glu Lys Pro Glu Val Ile
                420                 425                 430

Asp Ala Ser Glu Leu Thr Pro Ala Val Thr Thr Tyr Lys Leu Val Ile
            435                 440                 445

Asn Gly Lys Thr Leu Lys Gly Glu Thr Thr Thr Lys Ala Val Asp Ala
            450                 455                 460

Glu Thr Ala Glu His His Phe Lys Gln Tyr Ala Glu Asp Asn Gly Val
465                 470                 475                 480

Asp Gly Val Trp Thr Tyr Asp Asp Ala Thr Lys Thr Phe Thr Val Thr
```

```
                    485                 490                 495
Glu Met Val Thr Glu Val Pro Gly Asp Ala Pro Thr Glu Pro Glu Lys
                500                 505                 510

Pro Glu Ala Ser Ile Pro Leu Val Pro Leu Thr Pro Ala Thr Pro Ile
                515                 520                 525

Ala Lys Asp Asp Ala Lys Lys Asp Asp Thr Lys Lys Glu Asp Ala Lys
                530                 535                 540

Lys Pro Glu Ala Lys Lys Glu Asp Ala Lys Lys Ala Glu Thr Leu Pro
545                 550                 555                 560

Thr Thr Gly Glu Gly Ser Asn Pro Phe Phe Thr Ala Ala Leu Ala
                565                 570                 575

Val Met Ala Gly Ala Gly Ala Leu Ala Val Ala Ser Lys Arg Lys Glu
                580                 585                 590

Asp

<210> SEQ ID NO 12
<211> LENGTH: 593
<212> TYPE: PRT
<213> ORGANISM: Artificial Sequence
<220> FEATURE:
<223> OTHER INFORMATION: Protein G EHHD variant

<400> SEQUENCE: 12

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
                20                  25                  30

Ala Val Asp Ser Pro Ile Glu Asp Thr Pro Ile Ile Arg Asn Gly Gly
            35                  40                  45

Glu Leu Thr Asn Leu Leu Gly Asn Ser Glu Thr Thr Leu Ala Leu Arg
        50                  55                  60

Asn Glu Glu Ser Ala Thr Ala Asp Leu Thr Ala Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Ala Asp Ala Leu Ala Lys Ala Lys Ala Asp Ala Leu
                100                 105                 110

Lys Glu Phe Asn Lys Tyr Gly Val Ser Asp Tyr Tyr Lys Asn Leu Ile
                115                 120                 125

Asn Asn Ala Lys Thr Val Glu Gly Val Lys Asp Leu Gln Ala Gln Val
130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
                180                 185                 190

Tyr Gly Val Ser Asp Tyr His Lys Asn Leu Ile Asn Asn Ala Lys Thr
                195                 200                 205

Val Glu Gly Val Lys Asp Leu Gln Ala Gln Val Glu Ser Ala Lys
                210                 215                 220

Lys Ala Arg Ile Ser Glu Ala Thr Asp Gly Leu Ser Asp Phe Leu Lys
225                 230                 235                 240

Ser Gln Thr Pro Ala Glu Asp Thr Val Lys Ser Ile Glu Leu Ala Glu
                245                 250                 255
```

Ala Lys Val Leu Ala Asn Arg Glu Leu Asp Lys Tyr Gly Val Ser Asp
            260                 265                 270

Tyr Tyr Lys Asn Leu Ile Asn Asn Ala Lys Thr Val Glu Gly Val Lys
        275                 280                 285

Ala Leu Ile Asp Glu Ile Leu Ala Ala Leu Pro Lys Thr Asp Thr Tyr
290                 295                 300

Lys Leu Ile Leu Asn Gly Lys Thr Leu Lys Gly Glu Thr Thr Thr Glu
305                 310                 315                 320

Ala Val Asp Ala Glu Thr Ala Glu His His Phe Lys Gln Tyr Ala Asp
                325                 330                 335

Asp Asn Gly Val Asp Gly Glu Trp Thr Tyr Asp Asp Ala Thr Lys Thr
            340                 345                 350

Phe Thr Val Thr Glu Lys Pro Glu Val Ile Asp Ala Ser Glu Leu Thr
        355                 360                 365

Pro Ala Val Thr Thr Tyr Lys Leu Val Ile Asn Gly Lys Thr Leu Lys
370                 375                 380

Gly Glu Thr Thr Thr Glu Ala Val Asp Ala Glu Thr Ala Glu His His
385                 390                 395                 400

Phe Lys Gln Tyr Ala Asp Asp Asn Gly Val Asp Gly Glu Trp Thr Tyr
                405                 410                 415

Asp Asp Ala Thr Lys Thr Phe Thr Val Thr Glu Lys Pro Glu Val Ile
            420                 425                 430

Asp Ala Ser Glu Leu Thr Pro Ala Val Thr Thr Tyr Lys Leu Val Ile
        435                 440                 445

Asn Gly Lys Thr Leu Lys Gly Glu Thr Thr Thr Lys Ala Val Asp Ala
450                 455                 460

Glu Thr Ala Glu His His Phe Lys Gln Tyr Ala Asp Asp Asn Gly Val
465                 470                 475                 480

Asp Gly Val Trp Thr Tyr Asp Asp Ala Thr Lys Thr Phe Thr Val Thr
                485                 490                 495

Glu Met Val Thr Glu Val Pro Gly Asp Ala Pro Thr Glu Pro Glu Lys
            500                 505                 510

Pro Glu Ala Ser Ile Pro Leu Val Pro Leu Thr Pro Ala Thr Pro Ile
        515                 520                 525

Ala Lys Asp Asp Ala Lys Lys Asp Asp Thr Lys Lys Glu Asp Ala Lys
530                 535                 540

Lys Pro Glu Ala Lys Lys Glu Asp Ala Lys Lys Ala Glu Thr Leu Pro
545                 550                 555                 560

Thr Thr Gly Glu Gly Ser Asn Pro Phe Phe Thr Ala Ala Ala Leu Ala
                565                 570                 575

Val Met Ala Gly Ala Gly Ala Leu Ala Val Ala Ser Lys Arg Lys Glu
            580                 585                 590

Asp

<210> SEQ ID NO 13
<211> LENGTH: 1779
<212> TYPE: DNA
<213> ORGANISM: Artificial Sequence
<220> FEATURE:
<223> OTHER INFORMATION: Protein G EHH variant coding sequence

<400> SEQUENCE: 13
atggaaaaag aaaaaaaagt gaaatatttt ctgcgcaaaa gcgcgtttgg cctggcgagc        60
gtgagcgcgg cgtttctggt gggcagcacc gtgtttgcgg tggatagccc gattgaagat      120

```
accccgatta ttcgcaacgg cggcgaactg accaacctgc tgggcaacag cgaaaccacc     180
ctggcgctgc gcaacgaaga aagcgcgacc gcggatctga ccgcggcggc ggtggcggat     240
accgtggcgg cggcggcggc ggaaaacgcg ggcgcggcgg cgtgggaagc ggcggcggcg     300
gcggatgcgc tggcgaaagc gaaagcggat gcgctgaaag aatttaacaa atatggcgtg     360
agcgattatt ataaaaacct gattaacaac gcgaaaaccg tggaaggcgt gaaagatctg     420
caggcgcagg tggtggaaag cgcgaaaaaa gcgcgcatta gcgaagcgac cgatggcctg     480
agcgattttc tgaaaagcca gaccccggcg aagataccg tgaaaagcat gaactggcg      540 gaagcgaaag tgctggcgaa ccgcgaactg gataaatatg gcgtgagcga ttatcataaa     600
aacctgatta caacgcgaa  aaccgtggaa ggcgtgaaag atctgcaggc gcaggtggtg     660
gaaagcgcga aaaagcgcg  cattagcgaa gcgaccgatg gcctgagcga ttttctgaaa     720
agccagaccc cggcggaaga taccgtgaaa agcattgaac tggcggaagc gaaagtgctg     780
gcgaaccgcg aactggataa atatggcgtg agcgattatt ataaaaacct gattaacaac     840
gcgaaaaccg tggaaggcgt gaaagcgctg attgatgaaa ttctggcggc gctgccgaaa     900 accgataccct ataaactgat tctgaacggc aaaacccctga aaggcgaaac caccaccgaa    960
gcggtggatg cggaaaccgc ggaacatcat tttaaacagt atgcgaacga taacggcgtg     1020
gatggcgaat ggacctatga tgatgcgacc aaaaccttta ccgtgaccga aaaaccggaa     1080
gtgattgatg cgagcgaact gaccccggcg gtgaccacct ataaactggt gattaacggc     1140 aaaacccctga aggcgaaac  caccaccgaa gcggtggatg cggaaaccgc ggaacatcat     1200
tttaaacagt atgcgaacga taacggcgtg gatggcgaat ggacctatga tgatgcgacc     1260
aaaaccttta ccgtgaccga aaaaccggaa gtgattgatg cgagcgaact gaccccggcg     1320
gtgaccacct ataaactggt gattaacggc aaaacccctga aggcgaaac  caccaccaaa     1380 gcggtggatg cggaaaccgc ggaacatcat tttaaacagt atgcgaacga taacggcgtg     1440
gatggcgtgt ggacctatga tgatgcgacc aaaaccttta ccgtgaccga aatggtgacc     1500
gaagtgccgg cgatgcgcc  gaccgaaccg gaaaaaccgg aagcgagcat tccgctggtg     1560
ccgctgaccc cggcgacccc gattgcgaaa gatgatgcga aaaagatga taccaaaaaa      1620 gaagatgcga aaaaaccgga agcgaaaaaa gaagatgcga aaaagcgga acccctgccg      1680 accaccggcg aaggcagcaa cccgtttttt accgcggcgg cgctggcggt gatggcgggc     1740
gcgggcgcgc tggcggtggc gagcaaacgc aaagaagat                            1779
```

<210> SEQ ID NO 14
<211> LENGTH: 1779
<212> TYPE: DNA
<213> ORGANISM: Artificial Sequence
<220> FEATURE:
<223> OTHER INFORMATION: Protein G EHHE variant coding sequence

<400> SEQUENCE: 14

```
atggaaaaag aaaaaaaagt gaaatatttt ctgcgcaaaa gcgcgtttgg cctggcgagc      60
gtgagcgcgg cgtttctggt gggcagcacc gtgtttgcgg tggatagccc gattgaagat     120
accccgatta ttcgcaacgg cggcgaactg accaacctgc tgggcaacag cgaaaccacc     180
ctggcgctgc gcaacgaaga aagcgcgacc gcggatctga ccgcggcggc ggtggcggat     240
accgtggcgg cggcggcggc ggaaaacgcg ggcgcggcgg cgtgggaagc ggcggcggcg     300
gcggatgcgc tggcgaaagc gaaagcggat gcgctgaaag aatttaacaa atatggcgtg     360
```

-continued

| | |
|---|---|
| agcgattatt ataaaaacct gattaacaac gcgaaaaccg tggaaggcgt gaaagatctg | 420 |
| caggcgcagg tggtggaaag cgcgaaaaaa gcgcgcatta gcgaagcgac cgatggcctg | 480 |
| agcgattttc tgaaaagcca gaccccggcg aagataccg tgaaaagcat tgaactggcg | 540 |
| gaagcgaaag tgctggcgaa ccgcgaactg gataaatatg gcgtgagcga ttatcataaa | 600 |
| aacctgatta caacgcgaa aaccgtggaa ggcgtgaaag atctgcaggc gcaggtggtg | 660 |
| gaaagcgcga aaaagcgcg cattagcgaa gcgaccgatg gcctgagcga ttttctgaaa | 720 |
| agccagaccc cggcggaaga taccgtgaaa agcattgaac tggcggaagc gaaagtgctg | 780 |
| gcgaaccgcg aactggataa atatggcgtg agcgattatt ataaaaacct gattaacaac | 840 |
| gcgaaaaccg tggaaggcgt gaaagcgctg attgatgaaa ttctggcggc gctgccgaaa | 900 |
| accgatacct ataaactgat tctgaacggc aaaaccctga aggcgaaac caccaccgaa | 960 |
| gcggtggatg cggaaaccgc ggaacatcat tttaaacagt atgcggaaga taacggcgtg | 1020 |
| gatggcgaat ggacctatga tgatgcgacc aaaaccttta ccgtgaccga aaaaccggaa | 1080 |
| gtgattgatg cgagcgaact gaccccggcg gtgaccacct ataaactggt gattaacggc | 1140 |
| aaaaccctga aggcgaaac caccaccgaa gcggtggatg cggaaaccgc ggaacatcat | 1200 |
| tttaaacagt atgcggaaga taacggcgtg gatggcgaat ggacctatga tgatgcgacc | 1260 |
| aaaaccttta ccgtgaccga aaaaccggaa gtgattgatg cgagcgaact gaccccggcg | 1320 |
| gtgaccacct ataaactggt gattaacggc aaaaccctga aggcgaaac caccaccaaa | 1380 |
| gcggtggatg cggaaaccgc ggaacatcat tttaaacagt atgcggaaga taacggcgtg | 1440 |
| gatggcgtgt ggacctatga tgatgcgacc aaaaccttta ccgtgaccga aatggtgacc | 1500 |
| gaagtgccgg gcgatgcgcc gaccgaaccg gaaaaaccgg aagcgagcat tccgctggtg | 1560 |
| ccgctgaccc cggcgacccc gattgcgaaa gatgatgcga aaaagatga taccaaaaaa | 1620 |
| gaagatgcga aaaaccgga agcgaaaaaa gaagatgcga aaaagcgga acccctgccg | 1680 |
| accaccggcg aaggcagcaa cccgtttttt accgcggcgg cgctggcggt gatggcgggc | 1740 |
| gcgggcgcgc tggcggtggc gagcaaacgc aaagaagat | 1779 |

<210> SEQ ID NO 15
<211> LENGTH: 1779
<212> TYPE: DNA
<213> ORGANISM: Artificial Sequence
<220> FEATURE:
<223> OTHER INFORMATION: Protein G EHHD variant coding sequence

<400> SEQUENCE: 15

| | |
|---|---|
| atggaaaaag aaaaaaaagt gaaatatttt ctgcgcaaaa gcgcgtttgg cctggcgagc | 60 |
| gtgagcgcgg cgtttctggt gggcagcacc gtgtttgcgg tggatagccc gattgaagat | 120 |
| accccgatta ttcgcaacgg cggcgaactg accaacctgc tgggcaacag cgaaaccacc | 180 |
| ctggcgctgc gcaacgaaga aagcgcgacc gcggatctga ccgcggcggc ggtggcggat | 240 |
| accgtggcgg cggcggcggc ggaaaacgcg gcgcggcg cgtgggaagc ggcggcggcg | 300 |
| gcggatgcgc tggcgaaagc gaaagcggat gcgctgaaag aatttaacaa atatggcgtg | 360 |
| agcgattatt ataaaaacct gattaacaac gcgaaaaccg tggaaggcgt gaaagatctg | 420 |
| caggcgcagg tggtggaaag cgcgaaaaaa gcgcgcatta gcgaagcgac cgatggcctg | 480 |
| agcgattttc tgaaaagcca gaccccggcg aagataccg tgaaaagcat tgaactggcg | 540 |
| gaagcgaaag tgctggcgaa ccgcgaactg gataaatatg gcgtgagcga ttatcataaa | 600 |
| aacctgatta caacgcgaa aaccgtggaa ggcgtgaaag atctgcaggc gcaggtggtg | 660 |

-continued

```
gaaagcgcga aaaaagcgcg cattagcgaa gcgaccgatg gcctgagcga ttttctgaaa      720
agccagaccc cggcggaaga taccgtgaaa agcattgaac tggcggaagc gaaagtgctg      780
gcgaaccgcg aactggataa atatggcgtg agcgattatt ataaaaacct gattaacaac      840
gcgaaaaccg tggaaggcgt gaaagcgctg attgatgaaa ttctggcggc gctgccgaaa      900
accgatacct ataaactgat tctgaacggc aaaaccctga aaggcgaaac caccaccgaa      960
gcggtggatg cggaaaccgc ggaacatcat tttaaacagt atgcggatga taacggcgtg     1020
gatggcgaat ggacctatga tgatgcgacc aaaaccttta ccgtgaccga aaaaccggaa     1080
gtgattgatg cgagcgaact gaccccggcg gtgaccacct ataaactggt gattaacggc     1140
aaaaccctga aggcgaaac caccaccgaa gcggtggatg cggaaaccgc ggaacatcat     1200
tttaaacagt atgcggatga taacggcgtg gatggcgaat ggacctatga tgatgcgacc     1260 aaaacccttta ccgtgaccga aaaaccggaa gtgattgatg cgagcgaact gaccccggcg     1320
gtgaccacct ataaactggt gattaacggc aaaaccctga aaggcgaaac caccaccaaa     1380
gcggtggatg cggaaaccgc ggaacatcat tttaaacagt atgcggatga taacggcgtg     1440
gatggcgtgt ggacctatga tgatgcgacc aaaaccttta ccgtgaccga aatggtgacc     1500
gaagtgccgg gcgatgcgcc gaccgaaccg gaaaaaccgg aagcgagcat tccgctggtg     1560
ccgctgaccc cggcgacccc gattgcgaaa gatgatgcga aaaagatga taccaaaaaa     1620 gaagatgcga aaaaccgga agcgaaaaaa gaagatgcga aaaagcgga aaccctgccg     1680 accaccggcg aaggcagcaa cccgtttttt accgcggcgg cgctggcggt gatggcgggc     1740
gcgggcgcgc tggcggtggc gagcaaacgc aaagaagat                           1779
```